(12) United States Patent
Bailey et al.

(10) Patent No.: US 12,197,047 B2
(45) Date of Patent: Jan. 14, 2025

(54) CONTACT LENS

(71) Applicant: Ohio State Innovation Foundation, Columbus, OH (US)

(72) Inventors: Melissa D. Bailey, Gahanna, OH (US); Joseph T. Barr, Dublin, OH (US); Robin G. Sears, Dublin, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 571 days.

(21) Appl. No.: 17/440,616

(22) PCT Filed: Mar. 19, 2020

(86) PCT No.: PCT/US2020/023528
§ 371 (c)(1),
(2) Date: Sep. 17, 2021

(87) PCT Pub. No.: WO2020/191139
PCT Pub. Date: Sep. 24, 2020

(65) Prior Publication Data
US 2022/0163819 A1 May 26, 2022

Related U.S. Application Data

(60) Provisional application No. 62/820,318, filed on Mar. 19, 2019.

(51) Int. Cl.
*G02C 7/04* (2006.01)
*A61B 5/00* (2006.01)
(Continued)

(52) U.S. Cl.
CPC ............ *G02C 7/048* (2013.01); *A61B 5/0002* (2013.01); *A61B 5/6821* (2013.01); *A61B 5/742* (2013.01);
(Continued)

(58) Field of Classification Search
None
See application file for complete search history.

(56) References Cited

U.S. PATENT DOCUMENTS 3,828,777 A * 8/1974 Ness ................. A61F 9/0017
424/427
4,484,922 A * 11/1984 Rosenwald .......... A61F 9/0017
424/429
(Continued)

FOREIGN PATENT DOCUMENTS

CN 101506717 8/2009
CN 102621710 8/2012
(Continued)

OTHER PUBLICATIONS

Examination Report issued for Australian Application No. 2022202001, dated Apr. 12, 2023.
(Continued)

*Primary Examiner* — Darryl J Collins
(74) *Attorney, Agent, or Firm* — Meunier Carlin & Curfman LLC

(57) ABSTRACT

Disclosed herein is a contact lens. Some disclosed embodiments comprise a lenticular aspect. In some instances the lenticular aspect varies in at least one of thickness, distance from the edge of the contact lens, or lenticular height along its length. In one aspect, a superior portion of the lenticular aspect attaches to an upper eyelid of a wearer by at least a portion of the lenticular aspect interacting with an upper tarsal plate of the upper eyelid of a wearer.

24 Claims, 14 Drawing Sheets

(51) Int. Cl.
  *A61K 9/00* (2006.01)
  *A61K 38/13* (2006.01)
(52) U.S. Cl.
  CPC ............ *A61K 9/0051* (2013.01); *A61K 38/13* (2013.01); *G02C 7/04* (2013.01); *G02C 7/041* (2013.01); *G02C 7/049* (2013.01)

(56) References Cited

U.S. PATENT DOCUMENTS

| | | | |
|---|---|---|---|
| 4,573,775 A | 3/1986 | Bayshore | |
| 4,614,413 A | 9/1986 | Obssuth | |
| 4,666,267 A | 5/1987 | Wichterle | |
| 4,854,089 A * | 8/1989 | Morales | G02C 7/041 82/1.11 |
| 4,859,049 A | 8/1989 | Muller | |
| 4,896,958 A | 1/1990 | Ames et al. | |
| 5,056,908 A | 10/1991 | Cohen | |
| 5,104,213 A | 4/1992 | Wolfson | |
| 5,125,728 A | 6/1992 | Newman et al. | |
| 5,141,301 A | 8/1992 | Morstad | |
| 5,166,710 A | 11/1992 | Hofer et al. | |
| 5,245,366 A | 9/1993 | Svochak | |
| 5,296,880 A | 3/1994 | Webb | |
| 5,500,695 A | 3/1996 | Newman | |
| 5,532,768 A | 7/1996 | Onogi et al. | |
| 5,764,339 A | 6/1998 | Horton | |
| 5,912,719 A | 6/1999 | Baude | |
| 5,971,542 A | 10/1999 | Volker et al. | |
| 5,988,813 A | 11/1999 | Neadle et al. | |
| 6,092,899 A | 7/2000 | Wanders | |
| 6,109,749 A | 8/2000 | Bernstein | |
| 6,217,896 B1 | 4/2001 | Benjamin | |
| 6,409,339 B1 | 6/2002 | Wanders | |
| 6,491,392 B2 | 12/2002 | Roffman et al. | |
| 6,773,107 B2 | 8/2004 | Ye et al. | |
| 6,921,168 B2 | 7/2005 | Lindacher et al. | |
| 7,052,133 B2 | 5/2006 | Lindacher | |
| 7,080,906 B2 | 7/2006 | Lindacher | |
| 7,201,480 B2 | 4/2007 | Neadle et al. | |
| 7,384,143 B2 | 6/2008 | Hall et al. | |
| 7,543,935 B2 | 6/2009 | Ezekiel | |
| 7,560,056 B2 | 7/2009 | Van Gemert et al. | |
| 7,695,135 B1 | 4/2010 | Rosenthal | |
| 7,695,435 B2 | 4/2010 | Benson et al. | |
| 8,485,662 B2 | 12/2013 | Collins | |
| 8,864,306 B2 | 10/2014 | de Juan, Jr. et al. | |
| 9,823,493 B2 | 11/2017 | Caldarise et al. | |
| 10,175,504 B2 | 1/2019 | Goto et al. | |
| 10,191,302 B2 | 1/2019 | Bailey et al. | |
| 10,598,957 B2 | 3/2020 | Bailey | |
| 11,022,816 B2 | 6/2021 | Bailey et al. | |
| 11,022,817 B2 | 6/2021 | Bailey et al. | |
| 11,320,673 B2 | 5/2022 | Bailey et al. | |
| 2002/0075447 A1 | 6/2002 | Andino et al. | |
| 2003/0151718 A1 | 8/2003 | Marmo et al. | |
| 2004/0017542 A1 | 1/2004 | Lindacher et al. | |
| 2004/0057010 A1 | 3/2004 | Altmann | |
| 2004/0156013 A1 * | 8/2004 | Lindacher | A61F 2/1613 351/159.41 |
| 2005/0068489 A1 | 3/2005 | Hall et al. | |
| 2005/0099595 A1 | 5/2005 | Lindacher | |
| 2005/0251065 A1 | 11/2005 | Henning et al. | |
| 2006/0290883 A1 | 12/2006 | Rosenthal | |
| 2008/0013044 A1 | 1/2008 | Wanders | |
| 2008/0262812 A1 | 10/2008 | Arata et al. | |
| 2010/0153081 A1 | 6/2010 | Belletre et al. | |
| 2010/0245759 A1 * | 9/2010 | Legerton | G02C 7/041 351/159.05 |
| 2011/0249235 A1 | 10/2011 | Duis et al. | |
| 2012/0075581 A1 * | 3/2012 | Roffman | G02C 7/048 351/159.41 |
| 2012/0194778 A1 | 8/2012 | Skudder et al. | |
| 2012/0271599 A1 | 10/2012 | Lavallee et al. | |
| 2013/0208237 A1 * | 8/2013 | Hawke | G02C 7/049 351/159.36 |
| 2013/0258275 A1 | 10/2013 | Toner | |
| 2014/0063445 A1 | 3/2014 | Caldarise et al. | |
| 2016/0091737 A1 | 3/2016 | Kim et al. | |
| 2017/0082868 A1 | 3/2017 | Bailey et al. | |
| 2018/0129071 A1 | 5/2018 | Vidal et al. | |
| 2018/0313717 A1 | 11/2018 | Wang et al. | |
| 2019/0049749 A1 * | 2/2019 | Payor | G02C 7/083 |
| 2019/0391412 A1 | 12/2019 | Bailey et al. | |
| 2021/0382323 A1 | 12/2021 | Bailey et al. | |
| 2021/0382324 A1 | 12/2021 | Bailey | |
| 2023/0161179 A1 | 5/2023 | Raasch | |

FOREIGN PATENT DOCUMENTS

| | | |
|---|---|---|
| CN | 105629504 | 6/2016 |
| CN | 107811751 | 3/2018 |
| DE | 102010019961 A1 | 11/2011 |
| EP | 0102223 | 3/1984 |
| EP | 0887685 | 12/1998 |
| EP | 1879064 | 1/2008 |
| EP | 2388640 | 11/2011 |
| EP | 2622404 | 6/2018 |
| FR | 2582416 | 11/1986 |
| GB | 2401954 | 11/2004 |
| GB | 2497424 | 6/2013 |
| JP | S5953812 A | 3/1984 |
| JP | H09325304 A | 12/1997 |
| JP | 11-514753 | 12/1999 |
| JP | 2014-48666 | 3/2014 |
| TW | 201621406 A | 6/2016 |
| WO | 8907281 | 8/1989 |
| WO | 92/22845 | 12/1992 |
| WO | 97/16760 | 5/1997 |
| WO | 98/14820 | 4/1998 |
| WO | 01/44860 A1 | 6/2001 |
| WO | 2005050291 | 6/2005 |
| WO | 2015066616 | 5/2015 |
| WO | 2015194120 | 12/2015 |
| WO | 2018/057234 A1 | 3/2018 |
| WO | 2019/046714 A1 | 3/2019 |

OTHER PUBLICATIONS

Communication Pursuant to Article 94(3) EPC, issued for Application No. 18852131.4, dated May 25, 2023.
Office Action issued for Japanese Application No. 2019-515919, dated Apr. 5, 2022.
Israeli Patent Office. Office Action issued in Israeli Application No. 303151. Oct. 31, 2023. 5 pages.
European Patent Office. Extended European Search Report issued in European Application No. 23205582.2. Jan. 25, 2024. 9 pages.
Korean Intellectual Property Office. Final Office Action. Issued in Patent Application No. 10-2019-7011606. Jul. 27, 2022. 5 pages, including translation.
Brazilian Intellectual Property Office. Preliminary Office Action. Issued in Brazilian Patent Application No. BR112019005750-1. Aug. 31, 2022. 5 pages, including translation.
Intellectual Property Corporation of Malaysia. Examination Report. Issued in Malaysian Application No. PI 2019001627. Oct. 5, 2022. 2 pages.
U.S. Patent and Trademark Office. International Search Report and Written Opinion. Issued in PCT Application No. PCT/US2021/026409. Jul. 22, 2021. 17 pages.
Office Action issued for U.S. Appl. No. 16/642,982, dated Oct. 1, 2021.
Office Action issued for Korean Patent Application No. 10-2019-7011606, dated Jan. 17, 2022.
Notice of Alloawance issued for U.S. Appl. No. 16/642,982, dated Jan. 27, 2022.
English translation of Office Action for Vietnamese Application No. 1-2019-01975 dated Jun. 29, 2023.
English Summary of Office Action for Argentine Application No. 20190102352 dated Jun. 30, 2023.

(56) References Cited

OTHER PUBLICATIONS

English translation of Notice of Reasons for Refusal for Japanese Application No. 2022-192875 dated Aug. 8, 2023.
International Searching Authority (ISA/US). International Search Report and Written Opinion, issued in PCT Application No. PCT/US2020/023528 on Jun. 4, 2020. 11 pages.
International Search Report and Written Opinion issued for Application No. PCT/US2018/049084, dated Oct. 29, 2018.
International Preliminary Report on Patentability issued for Application No. PCT/US2018/049084, dated Mar. 12, 2020.
International Search Report and Written Opinion for Application No. PCT/US2017/048617. Mailed by the U.S. International Searching Authority on Nov. 8, 2017. 10 pages.
International Preliminary Report on Patentability issued for Application No. PCT/US2017/048617, dated Mar. 26, 2019, 7 pages.
Extended European Search Report issued by the European Patent Office in Application No. EP17853644.7 on May 26, 2020. 10 pages.
Communication Pursuant to Rule 164(1) EPC, issued for Application No. 18852131.4, dated May 21, 21, 11 pages.
Extended European Search Report, issued for Application No. 18852131.4, dated Sep. 21, 2021, 13 pages.
Examination Report issued by the Australian Intellectual Property Office in Australian Application No. 2017330483 on Feb. 1, 2021. 7 pages.
Office Action issued for Chinese Application No. 201780070220.3, dated Apr. 13, 2020. 13 pages including English translation.
Office Action issued for Chinese Application No. 201780070220.3, dated Sep. 14, 2020.
Office Action issued for Chinese Application No. 201780070220.3, dated Dec. 22, 2020. 19 pages.
Office Action issued for Chinese Application No. 201780070220.3, dated Jun. 28, 2021.
Office Action and Search Report issued by the Russian Patent Office in Russian Application No. 2019112014 on Dec. 14, 2020. 15 pages.
English Translation of Decision on Granting Russian Application No. 019112014/28(023349) dated Jul. 15, 2021.
Examination report issued for Indian Application No. 201917014551, dated Mar. 25, 2021.
Office Action issued for Japanese Application No. 2019-515919, dated Aug. 17, 2021.
Bennett, et al., Clinical Contact Lens Practice, 2005, Table 27.5. Biofocal/Multifocal Contact Lens Fitting Guidelines, p. 539.
Barr, Joseph T. "High Ametropia." Contact Lens Practice, edited by Nathan Efron, 2nd ed., Butterworth Heinemann Elsevier, 2010, pp. 298-302. (Year: 2010).
Kennard, D. W., and G. L. Smyth. "The causes of downward eyelid movement with changes of gaze, and a study of the physical factors concerned." The Journal of physiology 166.1 (1963): 178.
Kessing, Svend Vedel. "A new division of the conjunctiva on the basis of x-ray examination." Acta ophthalmologica 45.5 (1967): 680-683.
Messer, Prescribing for Astigmatism. Taming Those Tories. Feb. 1, 2016, 2 pages.
Polse, Kenneth A. "Contact Lens Fitting in Aphakia." American Journal of Optometry and Archives of American Academy of Optometry, Mar. 1969, pp. 213-219. (Year: 1969).
Quinn, Thomas G. "Avoiding the Low Riding Lens." Contact Lens Spectrum, Jul. 1, 2000, www.clspectrum.com/issues/2000/july- 2000/avoiding-the-low-riding-lens. (Year: 2000).
Rueff, et al., Presbyopic and non-presbyopic contact lens opinions and vision correction preferences, Contact Lens and Anterior Eye 40.5 (2017): 323-328.
Snyder, Christopher. "Designing Minus Carrier RGP Lenses." Contact Lens Spectrum, Dec. 1, 1998, www.clspectrum.com/issues/1998/december-1998/designing-minus-carrier-rgp-lenses. (Year: 1998).
Young, Graeme. "Mathematical model for evaluating soft contact lens fit." Optometry and Vision Science 91.7 (2014): e167-e176.
Raasch, T. Aberrations and spherocylindrical powers within subapertures of freeform surfaces. J. Opt. Soc. Am. A 28, 2642-2646 (2011).
Examination Report issued for Malaysian Application No. PI 2019001627, dated Oct. 5, 2022.
European Search Report issued for Application No. 20773904.6, dated Dec. 6, 2022.
Office Action issued for U.S. Appl. No. 17/331,079, dated Sep. 22, 2023.
Office Action issued for Canadian Application No. 3,038,057 dated Aug. 21, 2023.
Office Action issued for U.S. Appl. No. 17/331,059, dated Sep. 21, 2023.
European Patent Office. Extended European search report. Issued in EP Application No. 21784798.7 on Apr. 12, 2024. 9 pages.
European Patent Office. Communication pursuant to Article 94(3) EPC. Issued in EP Application No. 18852131.4 on Apr. 30, 2024. 5 pages.
Canadian Intellectual Property Office. Notice of Allowance. Issued in CA Application No. 3038057. Apr. 29, 2024. 1 page.
U.S. Patent & Trademark Office. Restriction Requirement. Issued in U.S. Appl. No. 29/729,365 on Jun. 10, 2024. 5 pages.
Intellectual Property Office of the Philippines. Substantive Examination Report. Issued in PH Application No. 1/2019/550043 on May 24, 2024. 6 pages.
Communication pursuant to Article 94(3) EPC in connection to EP Application No. 20 773 904.6, dated Sep. 10, 2024.
Search Report for Taiwan Application No. 113120559, dated Oct. 11, 2024.
Office Action in connection to KR Application No. 10-2023-7019444, dated Oct. 17, 2024.

\* cited by examiner

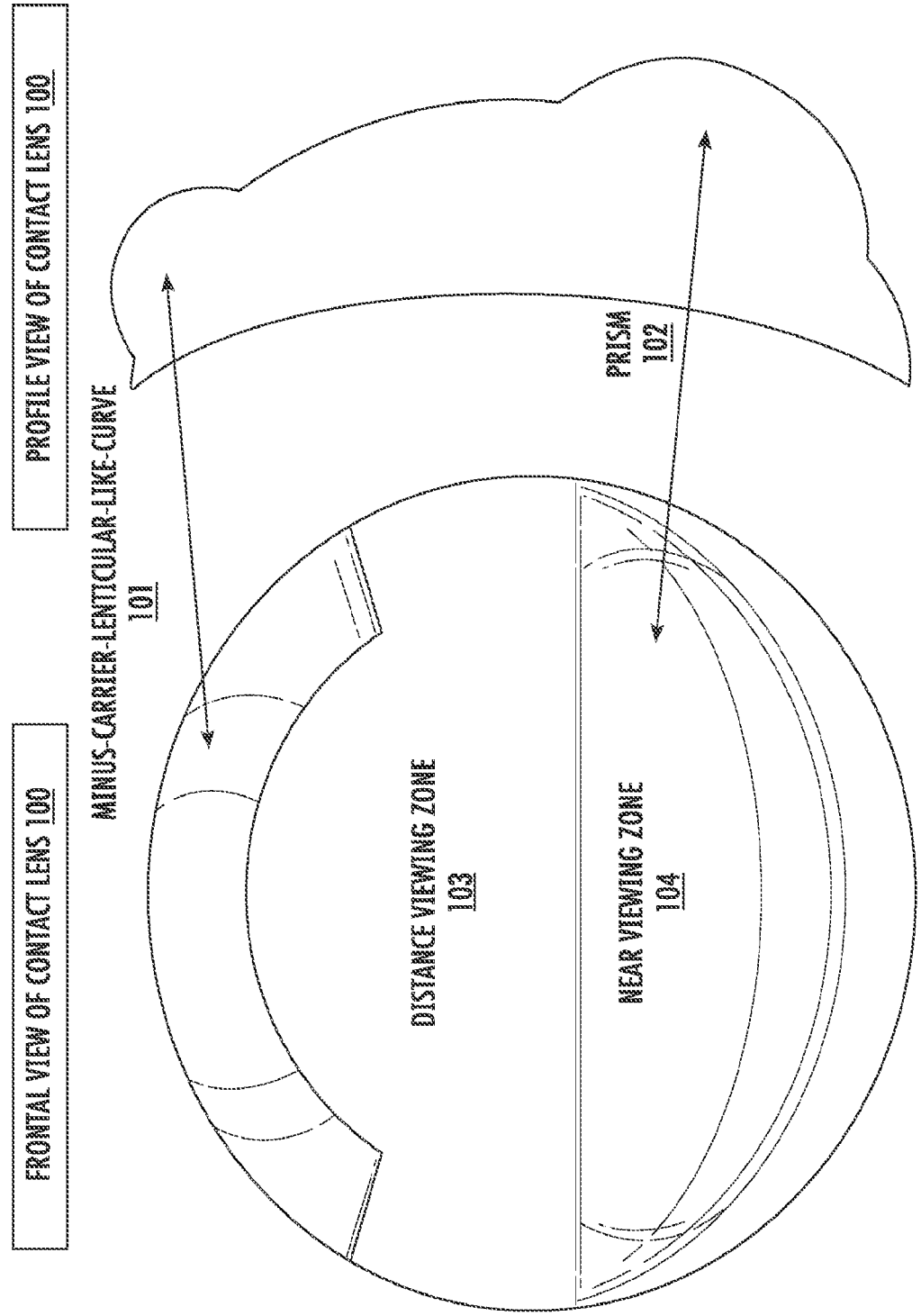

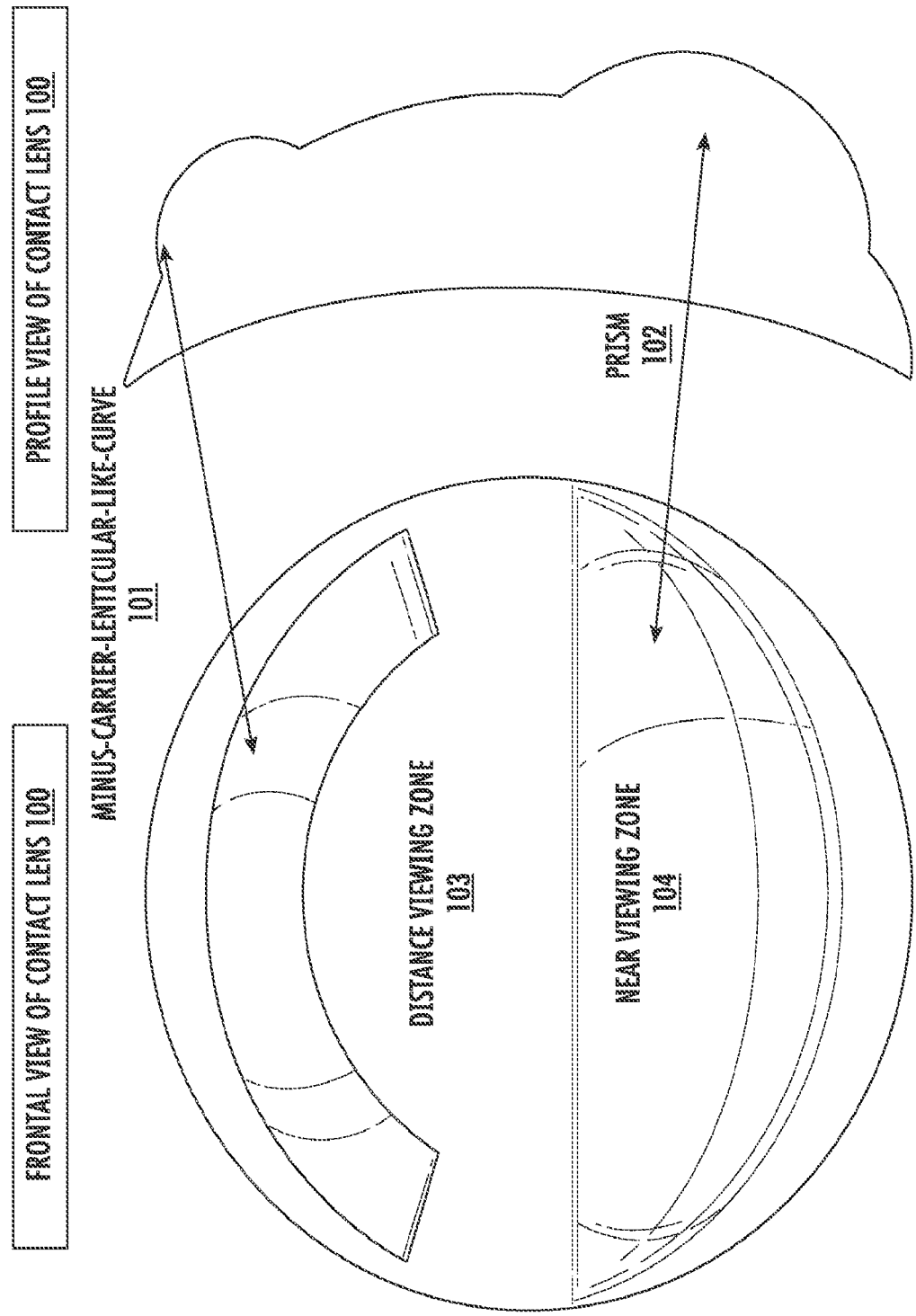

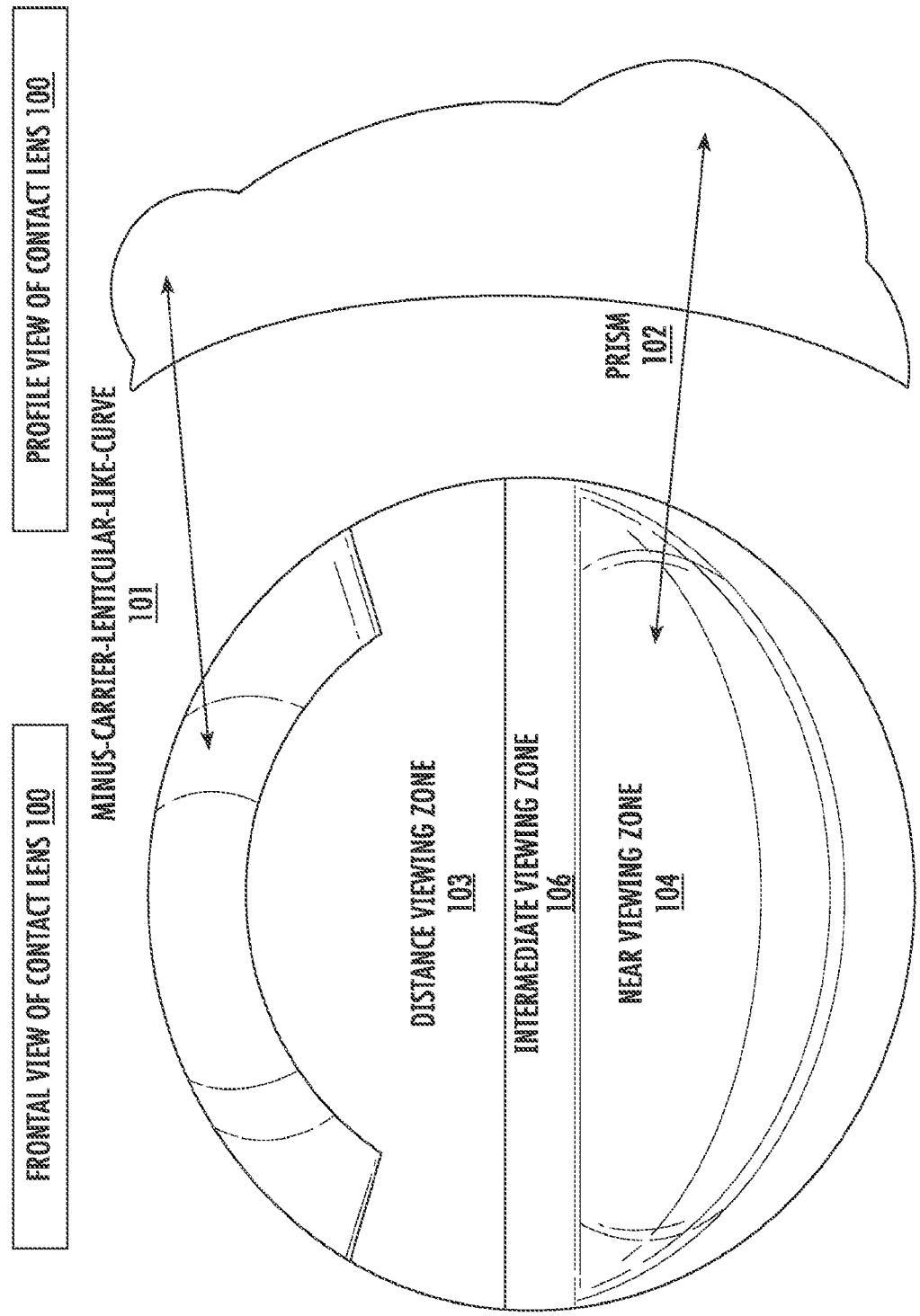

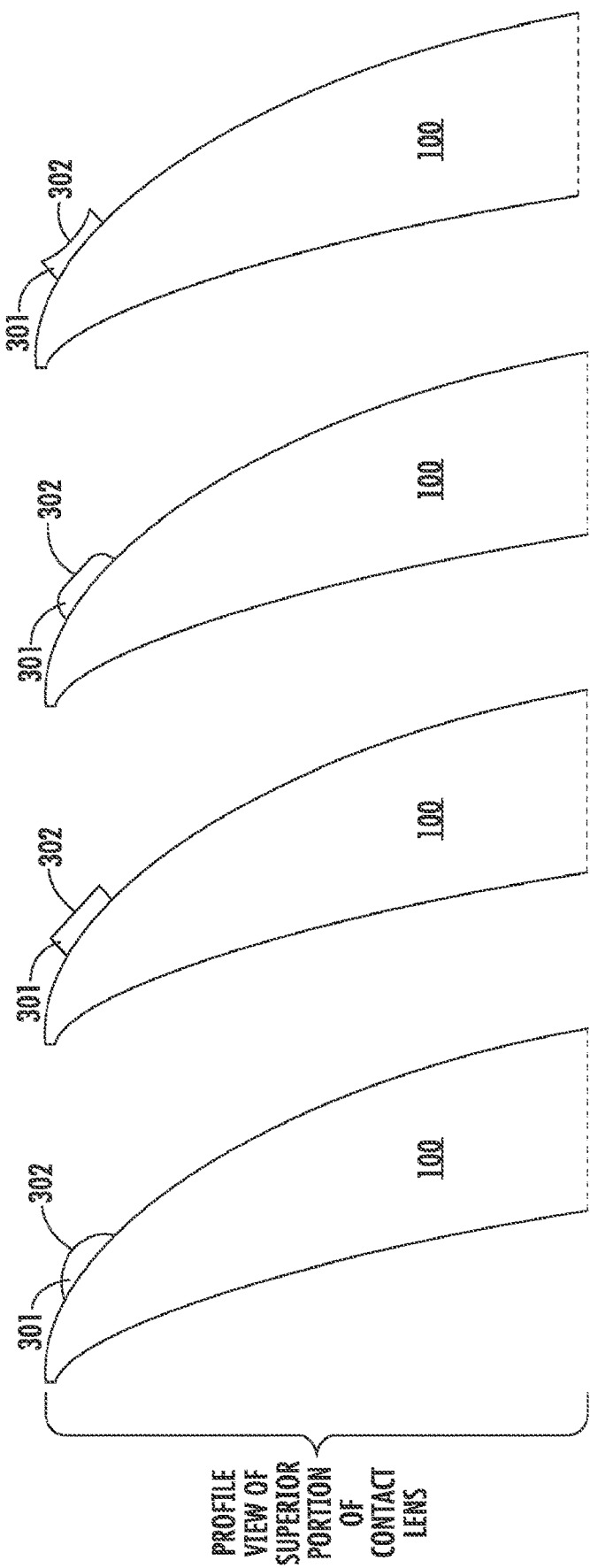

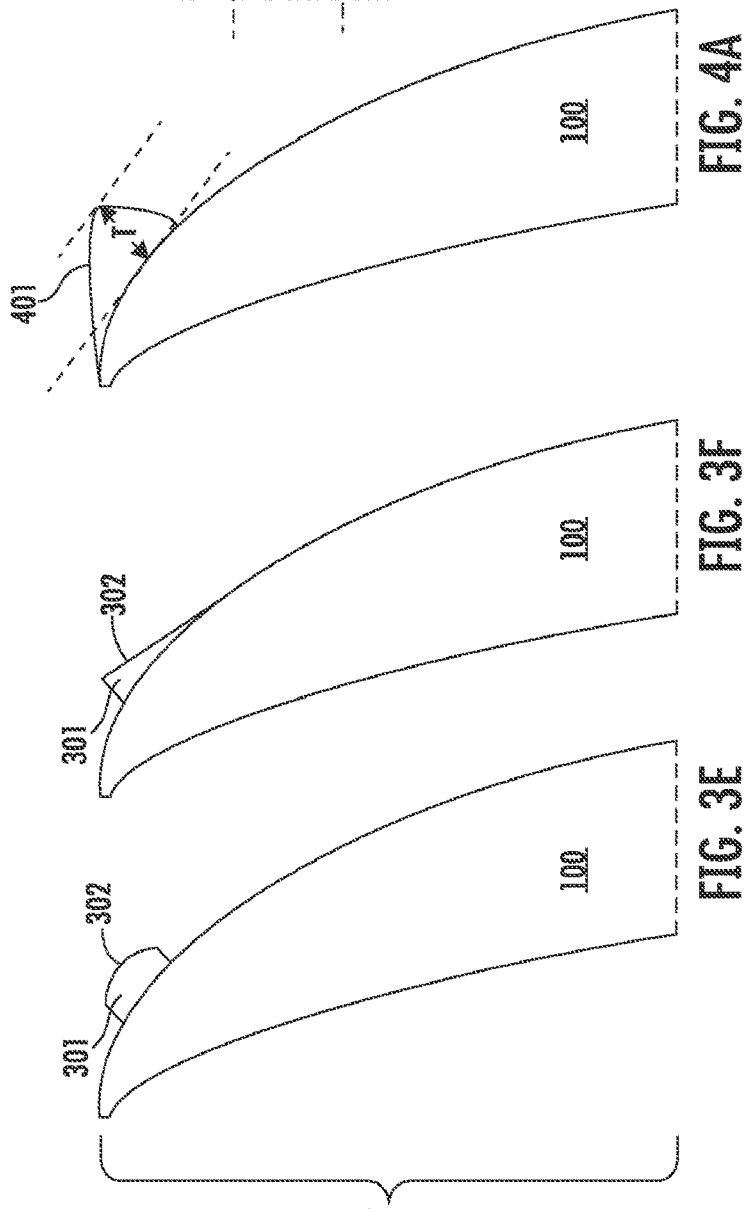
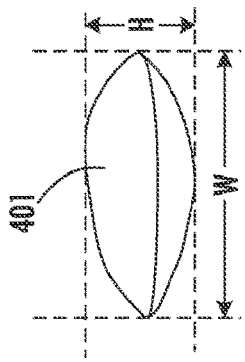
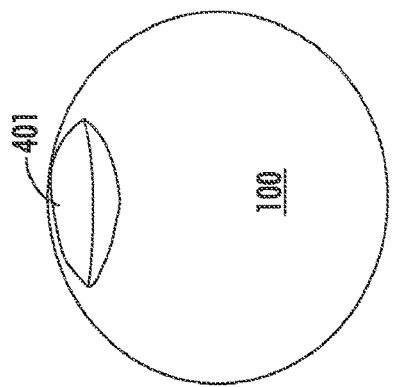

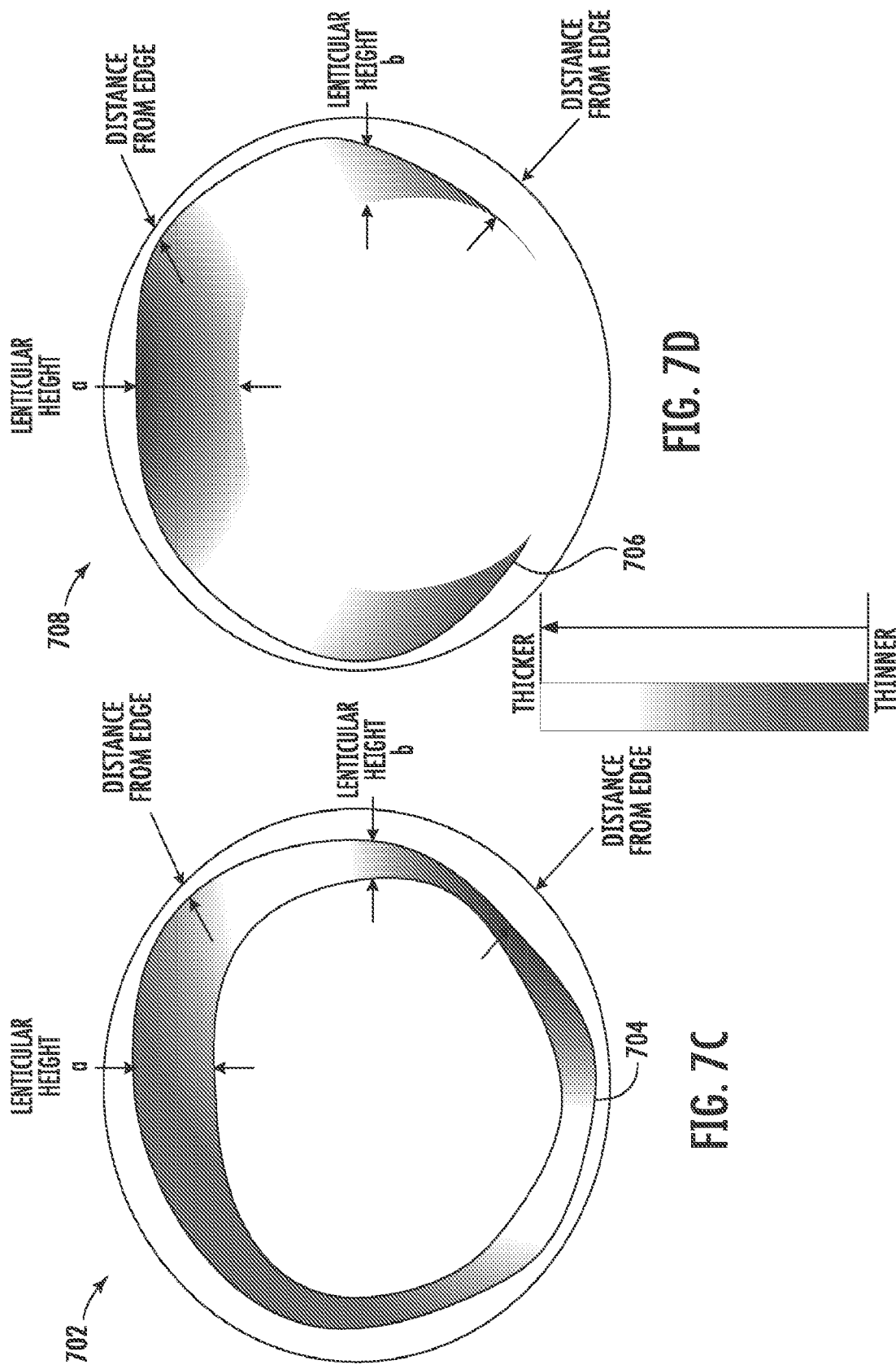

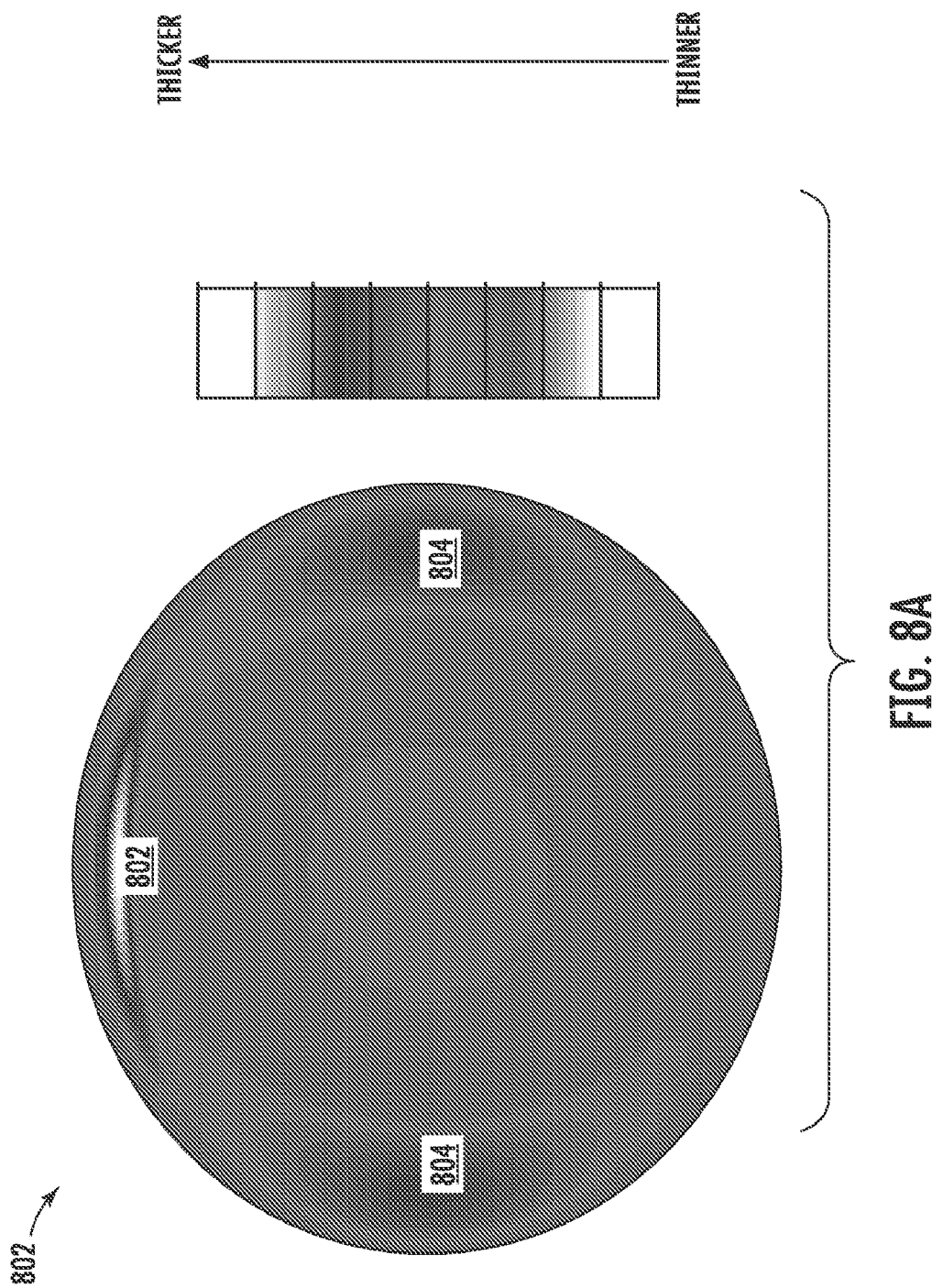

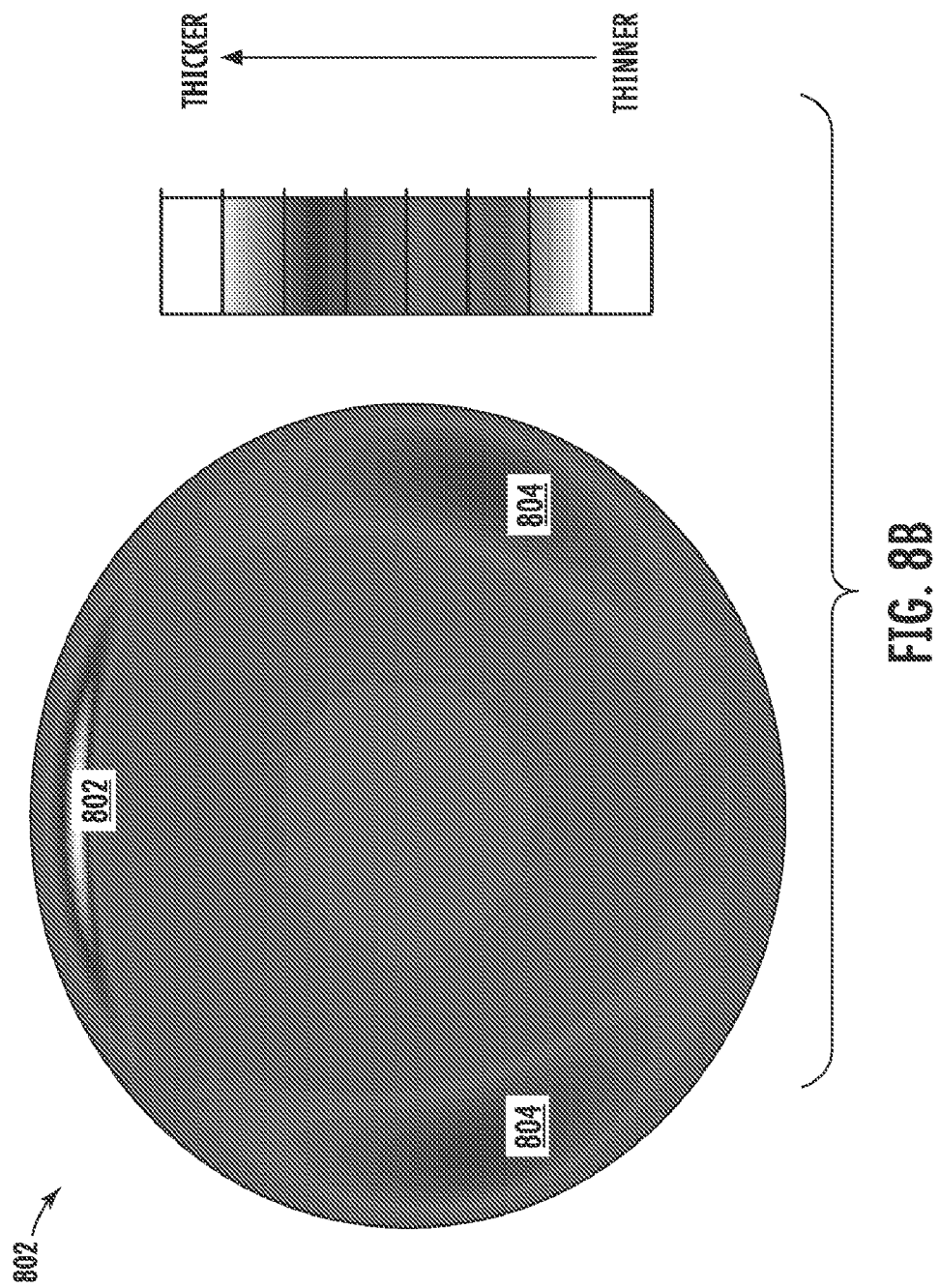

CONTACT LENS WITH
LENTICULAR COMPARTMENT

OVAL-SHAPED
CONTACT LENS

CONTACT LENS WITH
SCALLOPED EDGES

CONTACT LENS

CROSS REFERENCE TO RELATED APPLICATION

This application is a national stage application filed under 35 U.S.C. § 371 of PCT/US2020/023528 filed Mar. 19, 2020, which claims priority to and benefit of U.S. provisional patent application Ser. No. 62/820,318 filed Mar. 19, 2019, which is fully incorporated by reference and made a part hereof.

BACKGROUND

Traditionally, rigid gas permeable (RGP) contact lenses are fitted with a "lid attachment" fit by either using the naturally thicker edge of a minus-shaped RGP contact lens or by adding minus-carrier lenticular (a thicker edge tapered towards the junction with the front optic zone or, of constant thickness from the edge to the junction with the optic zone) to a plus-shaped RGP contact lens. The shape that is used in conventional RGP lenses was probably largely a function of what could be manufactured when lid attachment was first described in the 1970s. With these conventional RGP lens, the thicker edge required for lid attachment would be found 360-degrees around the lens periphery and is of the same thickness and/or height for the full 360-degrees. However, the lens does not necessarily need to be an RGP lens having that shape in order to achieve lid attachment (also referred to as being "suspended,") the lid attachment and the lens hanging off the upper lid, and other shapes and designs may provide a better fit that allows the contact lens to translate upwards in downgaze/and "articulation," where the eye moves downwards behind the contact as the lens is held in place by the upper eyelid. Translation of the lens/eye in downgaze would allow the use of a true bifocal, distance power in the upper, middle portion of the lens, and near power in the lower portion of the lens. In addition, the lid attachment fit provides rotational stabilization for toric lenses and other applications.

Furthermore, conventional soft contact lenses are designed such that they are "fitted" to the eye in a manner that they stay relatively stable during blinking, upgazes and downgazes. While this fitting helps maintain a wearer's vision, it often reduces tear exchange, tear layer thickness, and oxygen uptake of the cornea between the lens and the surface of the eye. If the contact lens is designed for a less "tight" fit to the eye (which can improve tear exchange, tear layer thickness, and oxygen uptake of the cornea), the lens will move during blinks, upgazes and downgazes, thus affecting the vision of the wearer, and excessive movement results in discomfort to the eye.

Therefore, what is desired are contact lenses that overcome challenges in the art, some of which are described above.

SUMMARY

Disclosed and described herein is a soft, rigid, or hybrid contact lens with a lid-attachment fit that is designed for enhanced tear exchange between the contact lens and the surface of the eye. The portion that is used for lid attachment (i.e., the lenticular aspect) is placed at the top (superior) portion of the contact lens or varies dimensionally (thickness of the lenticular aspect, distance of the lenticular aspect from the edge of the contact lens, lenticular height, etc.) along the length of the lenticular aspect. With modern manufacturing capabilities, any number of shapes can be implemented to achieve the lid attachment fit and/or varying dimension of the lenticular aspect. The lens may also be designed such that it allows for enhanced tear exchange, tear layer thickness, and oxygen levels in the tears between the lens and the surface of the eye. Such a design may include, for example, a "flatter" design (less sagittal depth) for the whole lens or one or more regions of the lens, one or more grooves in the surface of the contact lens that is in contact with the eye, holes and/or slits in the contact lens, or a "looser" fit in the eye. The central back-surface radius of the contact lens may be 1.00 diopter or greater flatter than the central corneal curvature of the wearer. For example, the central back-surface radius of the contact lens may be 1.50 D to 3.00 D flatter than the central corneal curvature of the wearer, paired with additional flattening of peripheral back surface of the lens. The flatter lens design may include regions that are specifically designed to conform to the anatomy of the cornea and sclera, including a peripheral flattening of the back surface of the lens in the areas that cover the peripheral cornea and sclera. For example, the contact lens may be designed such that it if the lenticular was omitted from the contact lens it would move more than what is typical for a soft contact lens, i.e., 1.5 mm or more, or decenter 1 mm or more, when in place on the wearer's eye without the lenticular, but with the lenticular having achieved a lid attachment fit, the lens still moves 1.5 mm or more when in place on the wearer's eye, but the movement is controlled by the attachment to the upper lid, making the lens stable between blinks and providing better vision and comfort than without the lenticular.

The present disclosure further relates to translating bifocal, trifocal, multifocal, or progressive addition contact lenses that also work when the cornea is spherical or toric. For rotational stabilization, the contact lenses disclosed herein have an advantage over conventional base-down prism, peri-ballasting, and dynamic stabilization in that the disclosed lenses use the interaction between the lenticular aspect described herein and the upper eyelid tarsal plate or other parts of the eye's anatomy to stabilize the contact lens and may also use the interaction between the base of an optional prism and the lower eyelid. Interactions between the lenticular aspect and one or both eyelids provides better stabilization in the lens designs disclosed herein. In some instances, the disclosed contact lens design allows for the contact lens to have a translational movement when the patient looks from straight ahead gaze into downgaze. Instead of pushing the base of the prism in the contact lens upwards with the lower eyelid, as much of the prior art attempts to do, this design pulls the contact lens upwards, or holds the contact lens in place, with the lenticular aspect. This is because in some instances the lenticular aspect allows the contact lens to use a "lid-attached" fit, wherein the lens stays with the upper lid as the patient looks downwards.

Disclosed and described herein are embodiments of a contact lens comprising an edge extending a circumference of the contact lens; a lenticular aspect having a length and extending along at least a portion of the circumference of the contact lens, wherein the lenticular aspect varies in at least one of thickness, distance from the edge, or lenticular height along its length. In various aspects, the contact lens may be a soft contact lens, a rigid gas permeable contact lens, or a hybrid contact lens.

Optionally or alternatively, the contact lens may further comprise a superior portion of the contact lens; an inferior portion of the contact lens; and a lens portion, wherein the lenticular aspect is shaped to interact with an upper tarsal plate of an upper eyelid of a wearer, said interaction translating the contact lens upwards in a downgaze of the wearer or holding the contact lens in an upwards position as a wearer's eye moves downwards behind the contact lens.

Also disclosed and described herein are embodiments of a soft contact lens comprising an edge extending a circumference of the soft contact lens; a lenticular aspect having a length, a thickness, a distance from the edge of the contact lens, and a lenticular height, wherein the length of the lenticular aspect extends along the full circumference of the contact lens.

Alternatively or optionally, the lenticular aspect varies in at least one of the thickness, the distance from the edge, or the lenticular height along its length.

Alternatively or optionally, the soft contact lens further comprises a superior portion of the soft contact lens; an inferior portion of the soft contact lens; and a lens portion, wherein at least a portion of the lenticular aspect is shaped to interact with an upper tarsal plate of an upper eyelid of a wearer, said interaction translating the soft contact lens upwards in a downgaze of the wearer or holding the contact lens in an upwards position as a wearer's eye moves downwards behind the contact lens.

Further disclosed and described herein are embodiments of a contact lens comprising a lenticular aspect, wherein the lenticular aspect provides rotational stabilization to the contact lens, and wherein the contact lens further comprises a holographic, painted, printed, etched, and/or tinted portions.

Alternatively or optionally, the lenticular aspect comprises a superior lenticular aspect located in a central, upper portion of the lens shaped to interact with an upper tarsal plate of an upper eyelid of a wearer such that the contact lens translates upward in a downgaze of the wearer to place a viewing zone of the contact lens over a pupil or cornea of the wearer.

Alternatively or optionally, the contact lens further comprises an edge extending a circumference of the contact lens, wherein the lenticular aspect has a length and extends along at least a portion of the circumference of the contact lens, wherein the lenticular aspect varies in at least one of thickness, distance from the edge, or lenticular height along its length.

In various aspects, the contact lens may be a soft contact lens, a rigid gas permeable contact lens, or a hybrid contact lens.

Also disclosed and described herein are embodiments of a contact lens comprising one or more ballast zones, wherein each of the one or more ballast zones have a mass and the mass of each of the one or more ballast zones is selected to locate a center of mass or a center of gravity of the contact lens.

In various aspects, the contact lens may be a soft contact lens, a rigid gas permeable contact lens, or a hybrid contact lens.

Alternatively or optionally, the contact lens further comprises a lenticular aspect, wherein the lenticular aspect provides rotational stabilization to the contact lens.

Alternatively or optionally, the lenticular aspect comprises a superior lenticular aspect located in a central, upper portion of the lens shaped to interact with an upper tarsal plate of an upper eyelid of a wearer such that the contact lens translates upward in a downgaze of the wearer to place a viewing zone of the contact lens over a pupil or cornea of the wearer.

Alternatively or optionally, the contact lens further comprises an edge extending a circumference of the contact lens, wherein the lenticular aspect has a length and extends along at least a portion of the circumference of the contact lens, wherein the lenticular aspect varies in at least one of thickness, distance from the edge, or lenticular height along its length.

Further disclosed herein are embodiments of a method of making a contact lens comprising fully molding all portions of the contact lens except an optical zone; and lathing the optical zone after the contact lens is molded to customize the optical zone for an individual.

Alternatively or optionally, the method comprises fully molding all portions of the contact lens except for the optical zone comprises forming a lenticular aspect in a portion of the lens.

Alternatively or optionally, the lenticular aspect is located in a superior portion of the contact lens and is shaped to interact with an upper tarsal plate of an upper eyelid of a wearer such that the contact lens translates upward in a downgaze of the wearer to place a viewing zone of the contact lens over a pupil or cornea of the wearer and the superior lenticular aspect provides rotational stabilization to the contact lens.

Alternatively or optionally, the contact lens further comprises an edge extending a circumference of the contact lens, wherein the lenticular aspect has a length and extends along at least a portion of the circumference of the contact lens, and the lenticular aspect varies in at least one of thickness, distance from the edge, or lenticular height along its length.

In various aspects, the contact lens may be a soft contact lens, a rigid gas permeable contact lens, or a hybrid contact lens.

Also disclosed herein are embodiments of a method of prescribing a continuum of contact lenses for a person over time, the method comprising determining physical characteristics of a contact lens for a person; determining initial optical characteristics of the contact lens for the person; prescribing at a first time the contact lens for the person, said contact lens having the physical characteristics and the initial optical characteristics; at one or more times after the first time: determining new optical characteristics of the contact lens for the person; and prescribing a new contact lens for the person, said new contact lens having the same physical characteristics and the new optical characteristics.

In various aspects, the physical characteristics of the contact lens include one or more of lens diameter, lens shape, sagittal depth of the lens, lenticular aspect thickness, lenticular aspect distance from edge, lenticular aspect height, lenticular aspect length, ballast zone size, weight and location, and lens tinting. The physical characteristics of the contact lens may be determined to provide comfort of the contact lens when in the person's eye and also fit of the lens in the wearer's eye to provide centration, rotational stability, and to translate the contact lens upwards in a downgaze of the person or holding the contact lens in an upwards position as the person's eye moves downwards behind the contact lens. In some aspects, the physical characteristics determine whether the contact lens is a spherical, toric, presbyopic, or toric presbyopic contact lens. Alternatively or optionally, the contact lens is first formed having the physical characteristics and is fully molded except an optical zone and the optical zone is lathed at a later time to customize optics for the person. In various aspects, the contact lens may be a soft contact lens, a rigid gas permeable contact lens, or a hybrid contact lens.

The description below sets forth details of one or more embodiments of the present disclosure. Other features, objects, and advantages will be apparent from the description and from the claims.

BRIEF DESCRIPTION OF THE DRAWINGS

The accompanying figures, which are incorporated in and constitute a part of this specification, illustrate several aspects described below.

FIGS. 1A and 1B are schematic diagrams providing frontal (FIG. 1A) and a profile view (FIG. 1B) of a bifocal contact lens according to lens designs disclosed herein. FIGS. 1A and 1B show a lenticular aspect 101 comprising a minus-carrier curved lenticular aspect located on or proximate the superior edge of the contact lens 100.

FIGS. 1C and 1D are schematic diagrams providing frontal (FIG. 1C) and a profile view (FIG. 1D) of an alternate bifocal contact lens according to lens designs disclosed herein. FIGS. 1C and 1D show a lenticular aspect 101 comprising a minus-carrier curved lenticular aspect located further toward the center of the contact lens away from the superior edge of the contact lens 100.

FIGS. 1E and 1F are schematic diagrams providing frontal (FIG. 1E) and a profile view (FIG. 1F) of a multifocal lens comprising a distance viewing zone, a near viewing zone, and an intermediate zone located between the distance viewing zone and the near viewing zone.

FIGS. 3A-3F are profile schematic images of exemplary contact lens having various shaped lenticular aspects in a superior portion of the contact lens.

FIG. 4A is a profile schematic image of exemplary contact lens having an exemplary anatomically-shaped lenticular aspect in a superior portion of the contact lens.

FIG. 4B is a front view of the anatomically-shaped lenticular aspect of FIG. 4A showing width (w) and height (h) dimensions.

FIG. 4C is a front view of a contact lens having an anatomically-shaped lenticular aspect in a superior portion of the contact lens.

FIG. 5A shows that the embodiments described herein allow for a thicker tear film.

FIG. 7C is an illustration of a contact lens having a lenticular aspect that extends the full circumference of the contact lens and varies in lenticular height, distance from edge and thickness along its length.

FIG. 7D is an illustration of a contact lens having a lenticular aspect that does not extend the full circumference of the contact lens but varies in lenticular height, distance from edge and thickness along its length.

FIGS. 8A and 8B are grey-scale illustrations of a contact lens having a superior lenticular aspect and further comprising one or more ballast regions.

DETAILED DESCRIPTION

Figure 2:
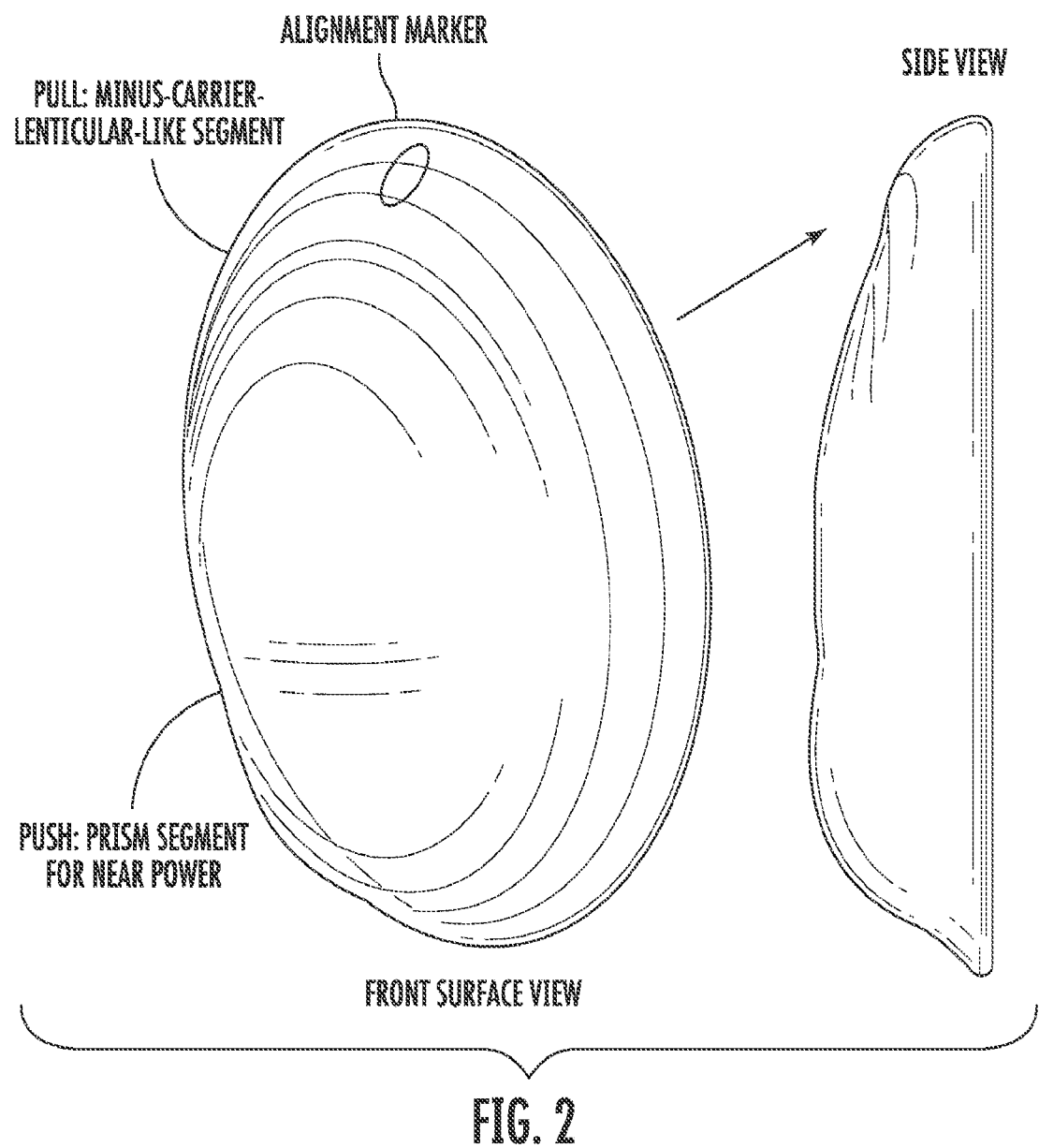
FIG. 2 illustrates schematic diagrams of a contact lens showing a "push" and "pull" mechanism associated with a lenticular aspect and an optional prism segment located in an inferior region of the contact lens.

The present disclosure now will be described more fully hereinafter with reference to specific exemplary embodiments. Indeed, the present disclosure can be embodied in many different forms and should not be construed as limited to the embodiments set forth herein.

Disclosed herein is a contact lens comprising a lenticular aspect located in a portion of the lens. For example, the lenticular aspect may extend over an upper (superior) portion of the lens and at least a portion of the lenticular aspect be shaped to interact with an upper tarsal plate of an upper eyelid of a wearer. For example, the lenticular may comprise a rounded, minus-carrier, curved lenticular aspect over a central, upper portion of the contact lens, though other lenticular shapes, designs and locations are contemplated as are various shapes, designs and uses of the contact lens.

The various embodiments of a contact lens disclosed herein generally comprise a lenticular aspect design that creates: (1) rotational stability of the contact lens in all gazes, (2) upwards translation, or movement, of the contact lens when the eye is in downward gaze, and/or holding the contact lens in a straight-ahead position as the eye moves into downward gaze behind the contact lens (3) a general, centered placement of the contact lens over the cornea and the pupil as needed as the person's gaze changes, and (4) enhanced tear exchange, a greater tear layer thickness, or increased oxygen uptake of a cornea of a wearer. "Upwards translation of the contact lens when the eye is in downward gaze" means that the contact lens is held in an upwards position when the patient looks down. The embodiments disclosed and described herein include one or more lenticular aspects located in a portion of the contact lens where the lenticular aspect has any shape that would allow the contact lens to attach itself to a lid of a wearer.

Referring to FIGS. 1A and 1B, a schematic diagram of frontal (FIG. 1A) and profile view (FIG. 1B) of a contact lens 100 according to lens designs disclosed herein is illustrated. The embodiment of a contact lens shown in FIGS. 1A and 1B is a bifocal lens in that is has a distance viewing zone 103 and a near viewing zone 104, though it is to be appreciated that embodiments described herein are equally applicable to monovision contact lens as well as bifocal and/or other multi-focal contact lens. In some instances, the contact lens may also have an intermediate zone 106 located between the distance viewing zone 103 and the near viewing zone 104. One of the features of the contact lens shown in FIGS. 1A and 1B is the placement of a lenticular aspect 101 over the upper, central portion of the contact lens. As described herein, the upper portion of the contact lens 100 is referred to as the superior portion and the lower portion of the contact lens 100 is referred to as the inferior portion. Generally, in the embodiment shown in FIGS. 1A and 1B, the lenticular aspect 101 is located completely in the superior portion of the contact lens 100 above a horizontal midline that passes through the center of the contact lens 100; however, the ends of one or more of the lenticular aspect may extend into the inferior portion of the contact lens that lies below the horizontal midline. In the embodiment shown in FIGS. 1A and 1B, the lenticular aspect 101 comprises a rounded, minus-carrier curved lenticular aspect that extends in an arc around a portion of the upper edge of the contact lens 100, though other shapes, sizes and designs of lenticular aspects 101 are contemplated within the scope of embodiments of this invention and disclosed herein. Another feature of the design shown in FIGS. 1A and 1B is the (optional) possible use of a prism 102 or a ballast in the lower portion of the contact lens 100. The combined features of the contact lens 100 disclosed herein provide rotational stabilization, translation, and/or centration. The lens can be made of a material that can sense light activity or molecules in the ocular environment and that contains elements that modulate light or the surrounding ocular environment, i.e., liquid crystal displays, filters, photochromatic materials, compartments containing other materials, or sensors. Though shown in FIGS. 1A and 1B as bifocal lens, it is to be appreciated that the contact lens 100 described herein can be of any vision-correction type including single-vision, bifocal, trifocal, progressive addition bifocal, multifocal, and/or toric, or for cosmetic lens. The lens and/or the lenticular aspect 101 can be hard, soft, RGP, and the like. The contact lens 100 and/or lenticular aspect 101 can be made of the same material as the contact lens 100, or of different materials. For example, the contact lens 100 may be made of hard or RGP material, while the lenticular aspect(s) 101 are comprised of soft material.

In FIGS. 1A, 1B, 1C and 1D, the lenticular aspect 101 can be seen at the top of the contact lens 100. The lenticular aspect 101 (in this example a minus-carrier curved lenticular aspect) can be placed at the upper edge of the soft contact lens 100, as seen in FIG. 1B, or can be located some distance from the edge of the contact lens 100, as can be seen in FIG. 1D. For example, the lenticular aspect 101 can be located in the central, upper portion of the contact lens 100. The lenticular aspect 101 can be 0.1, 0.2, 0.3, 0.4, 0.5, 0.6, 0.7, 0.8, 0.9, 1.0, 1.5, 2.0, 2.5, 3.0, 3.5, 4.0, 4.5, or 5.0 millimeters, or more, less, or any amount in-between, away from the outer edge of the contact lens 100. Optionally, a prism 102 or ballast can be located on the lens (for example, in the lower half of the contact lens 100). The use of prisms and/or ballast zones is discussed in more detail herein.

The current state-of-the-art in translating contact lenses is a rigid gas permeable (RGP) contact lens. There are currently no successful soft contact lenses that achieve translating vision. All of the prior art in translating soft contact lenses moves in the opposite direction of the designs described and shown herein, i.e., all other designs attempt to thin the upper portion of the contact lens as much as possible, rather than making it thicker and attached to the upper lid. The contact lenses disclosed herein provide a translating contact lens, including a soft contact lens, which is more comfortable and requires less adaptation time than conventional lens including conventional RGP lenses.

Generally speaking, patients are more willing and able to wear a soft contact lens than a rigid gas permeable contact lens, and a soft contact lens requires less expertise to fit. The current state-of-the-art in bifocal or multifocal soft contact lenses is simultaneous vision. In these lenses, both the rays focusing the distance vision and the rays focusing the near vision are within the pupil at the same time. Thus, the patient must be able to ignore the rays that are not in focus. This leads to some degradation of vision. In some aspects, the translating soft contact lens disclosed herein allows only light from one distance to be in focus at a time, providing clearer discreet vision at each distance.

The other current state-of-the-art option for fitting presbyopic patients in some conventional contact lenses is called monovision. In this case, one eye is powered for distance vision (usually the dominant eye) and one eye is powered for near vision (usually the non-dominant eye). Some patients are unable to adapt to this type of lens, again, especially when the patient requires a greater reading add power, because the difference between the two eyes becomes too uncomfortable. Also, it is well established that monovision correction in contact lenses or laser vision correction leads to a loss of depth perception. The translating contact lens disclosed herein allows for the use of higher reading add powers without degradation of the quality of distance vision. Because both eyes are fully and equally corrected at distance and near in the disclosed design, there is no induced loss of depth perception. The translating contact lens disclosed herein can also have an optical segment that provides a gradient of power change between the distance and near segments.

The contact lens disclosed herein are designed to suit many practical purposes. For example, in both rigid and soft contact lenses, the lens designs disclosed herein provide rotational stabilization in all gazes for toric contact lens designs, contact lenses designed to correct for various types of ocular aberration beyond a spherical correction, for electronically-generated and/or virtual optically displayed images, and/or bifocal or multifocal contact lenses. Additionally, the lens designs disclosed herein create upwards translation of a bifocal/multifocal contact lens in downward gaze. Furthermore, the lens designs disclosed herein achieve a "lid attached" fit similar to some conventional rigid gas permeable contact lens, i.e., keep the contact lens attached under the upper lid before, during, and after a blink.

In one embodiment, the upper portion of the contact lens interacts with an upper eyelid of the wearer. The upper portion of the contact lens that interacts with the upper lid can comprise 5, 10, 15, 20, 25, 30, 35, 40, 45, 50, 55, 60, 65, 70, or 75% of the area between the upper edge of the contact lens and the geometric center of the contact lens. For example, the area of the upper portion of the contact lens (meaning the "top half" of the contact lens, or the area between the upper edge and geometric center of the contact lens) that interacts with the upper lid can comprise 10 to 50% of the upper area of the lens.

Conventionally, a minus carrier lenticular that extends 360-degrees around the lens periphery and is of the same thickness and/or height for the full 360-degrees can be used in rigid gas permeable contact lenses in order to create a lid attached fit in a plus-shaped contact lens. In the contact lens designs disclosed herein, a lenticular aspect 101 is placed in the central, upper portion of the lens, rather than over a larger portion of the lens circumference, or varies dimensionally along the length of the lenticular aspect. Some embodiments of the contact lens designs disclosed herein have a smaller area where a relatively thick edge is present to interact with the upper eyelid margin, and the minimal presence of the lenticular aspect improves comfort over a more traditional minus carrier lenticular that would ordinarily be placed over the entire lens circumference and would have a constant thickness, distance from the contact lens's outer edge and lenticular height. There is enough surface area and thickness of the lenticular aspects present in some of the contact lens disclosed herein; however, to interact with the palpebral conjunctiva and upper tarsal plate that lies below it to assist with centration and rotational stability.

As shown in FIG. 2, and referred to herein as a "push" and a "pull" mechanism, in addition to the upper eyelid interacting with the lenticular, the upper eyelid can also interact with an optional prism in the lower portion of the contact lens according to the lens designs disclosed herein. The edge of the upper eyelid squeezes the thicker, base of the prism of the contact downwards with each blink. The base of the prism also interacts with the lower eyelid with each blink; therefore, the base of the prism is placed above the lower contact lens margin, high enough to remain above the lower eyelid when the eye is open. Just as multiple base curve options are available for fitting different corneal curvatures, multiple heights of the prism base are optionally used to account for differences in aperture size and position of the eyelids. In addition, multiple overall diameters of the contact lens can also be used. In other words, the prism portion can provide a change in power from the central optic zone of the contact lens. The base of the prism may not slide more than 1, 1.5, 2, 2.5, or 3 millimeters (mm) behind the lower lid, when the patient is looking straight ahead and/or downwards when the eye is open and during the blink.

As disclosed above, the lenticular aspect comprises a relatively thick area compared to the remaining portion of the contact lens. This area of thickness can be 1.5, 2, 3, 4, 5, 6, 7, 8, 9, or 10 times thicker than the remaining "non-thick" portions of the contact lens, and the thickness may vary over the length of the lenticular aspect. For example, the relatively thick area can comprise a thickest portion, which is 1.5 to 10 times thicker than the remaining center portion and/or optical zone of the contact lens.

The embodiments of contact lens disclosed herein can be used in the correction of ametropia (myopia, hyperopia, astigmatism, and/or higher order aberrations) in patients with or without presbyopia, i.e., a reading add that moves upwards through translation, in patients with other accommodative disorders, and/or patients with a binocular vision disorder can also be provided in the lens designs disclosed herein. Presbyopia affects approximately 100% of the population who live long enough (approximately 45 years of age) to develop the condition. The embodiments of contact lens disclosed herein can also treat other accommodative disorders, or binocular vision disorder. In some instances, embodiments of the contact lens disclosed herein can be used to display an electronically-generated and/or other virtual optically-displayed image.

Conventional contact lenses provide very limited options in terms of design parameters such as diameter and curvature. The disclosed contact lenses achieve translation in contact lens including soft contact lens. Soft contact lens are typically only feasible to manufacture in two base curve options, and very few are offered in multiple diameters. These multiple options in these two parameters in addition to the ability to vary the prism height, size, amount, or axis are optionally considered in the lens designs disclosed herein. Back or front surface toricity takes advantage of a toric, rather than spherical, corneal shape that occurs in some patients with astigmatism. The lenses disclosed herein still work when the cornea is spherical (not toric). The described lenses also have an advantage over base-down prism, peri-ballasting, and dynamic stabilization in that it in some embodiments the lens optionally uses a lenticular aspect described herein to use the upper eyelid tarsal plate to stabilize the contact lens in addition to the prismatic interaction of the lower lid (in lenses having an inferior prism or ballast). Interactions with both lids can provide better stabilization.

FIGS. 3A-3F are profile schematic images of exemplary contact lens having various shaped lenticular aspects in a superior portion of the contact lens. Each of the lenticular aspects 301 have a shaped top surface 302. In FIG. 3A, the lenticular aspect 301 comprises a rounded, minus-carrier, curve 302 over a central, upper portion of the lens. As described herein, the lenticular aspect may be on or proximate to the edge of the contact lens 100, or set back further away from the edge of the lens 100. Further, the lens 100 may include a single lenticular aspect 301, or it can be a plurality of lenticular aspects having various shapes, sizes and designs. FIGS. 3B-3F illustrate non-limiting examples of profiles of various other lenticular aspects including a flat-topped 302 lenticular aspect 301 (FIG. 3B), a lenticular aspect 301 having a flat top with rounded edges 302 (i.e., a "bump") (FIG. 3C), a lenticular aspect 301 having a concave top 302 (FIG. 3D), a lenticular aspect 301 having a convex top 302 (FIG. 3E), and a lenticular aspect 301 having a tapered top 302 shape that is thicker closer to the edge of the contact lens and which gradually thins toward the center of the contact lens (FIG. 3F). It is to be appreciated that the lenticular aspects 301 shown in FIGS. 3A-3F are intended to be non-limiting and are for exemplary purposes only. It is contemplated that the lenticular aspects of this invention are not limited by shape, size, number, position, or location.

FIG. 4A is a profile schematic image of exemplary contact lens having an exemplary anatomically-shaped lenticular aspect in a superior portion of the contact lens. In this embodiment, the lenticular aspect is shaped specifically to fit into a conjunctival sac and attach to the upper eyelid of the wearer. For example, the lenticular aspect of FIG. 4A is designed to fit within Kessing's Space of the wearer's upper eyelid (see, Kessing, Svend V., "A New Division of the Conjunctiva on the Basis of X-Ray Examination," Acta Ophthalmologica Vol. 45, 1967, which is fully incorporated by reference.) FIG. 4B is a front view of the anatomically-shaped lenticular aspect 401 of FIG. 4A showing width or length (w) and height (h) dimensions. In one of the embodiments, the anatomically-shaped lenticular aspects 401 shown in FIGS. 4A and 4B is shaped and sized in accordance with the conjunctival inserts disclosed and described in U.S. Pat. No. 6,217,896, which is fully incorporated by reference. In addition, rather than having the thickest portion of the lens or lenticular placed at the very edge of the contact lens, some exemplary contact lenses show the thickest portion of the lenticular placed where the conjunctiva overlying the tarsal plate meets with the lid wiper or margin of the upper eye lid.

Although volumetric and linear dimensions vary between individuals, human inferior conjunctival sacs have certain generally common features: a crescent shape horizontally; a thick inferior horizontal ridge and a wedge-like shape sagittally. In order to maximally utilize the actual volume and shape that could be contained in human conjunctival sacs, the anatomically-shaped lenticular aspect 401 can be of a crescent shape in the horizontal plane, with the central back curvature conforming to the bulbar surface (radius of back curvature approximately 14 mm, range 12-18 mm). Most of the volume of the device is contained in the inferior 50% of the shape, within a horizontal ridge situated approximately ⅔ of the way from the top of the lenticular aspect 401 and ⅓ of the way from the bottom of the lenticular aspect 401. The maximum thickness of this ridge, being of a crescent shape in the horizontal plane, is a dimension noted in the table (Table I), below. The front surface of the lenticular aspect 401 is more curved than the back in order to attain the crescent shape. The lenticular aspect 401 tapers superiorly above the ridge, so as to situate between the tarsal plate and the globe, so that the anatomically-shaped lenticular aspect 401 thins to an acute angle at its superior edge. Therefore, in the sagittal plane the lenticular aspect 401 appears wedge-like above the ridge, such that pressure of the inferior margin of the upper eyelid will induce a "minus-carrier" effect and help to contain the lenticular aspect 401 inside the cul-de sac. From the middle of the thicker volume in the ridge, the lenticular aspect 401 tapers to blunt points nasally and temporally, such that the lenticular aspect 401 is anchored within the tissue more tightly bound at the canthi. The horizontal length (w) of the lenticular aspect 401 is a dimension, covered in Table I, which is measured along the back surface of the lenticular aspect 401 from left to right behind the ridge. At the bottom, the lenticular aspect 401 is rounded from left to right (radius of curvature approximately 22 mm, range 20-25 mm) and from front to back (radius of curvature approximately 0.75 mm, range 0.5-1.0 mm in the middle) with the most inferior portion of the lenticular aspect 401 at the horizontal middle.

Below, Table I provides exemplary dimensions for three sizes of an anatomically-shaped lenticular aspect 401 (refer to FIGS. 4A and 4B).

TABLE I

DIMENSIONS OF THREE DESIGNS OF AN ANATOMICALLY-SHAPED LENTICULAR

| DIMENSIONS | Three Designs by Size | | |
|---|---|---|---|
| | LARGE | MEDIUM | SMALL |
| Volume (μl) | 160 | 110 | 60 |
| Max. Horizontal Width/Length (W) (mm) | 26.75 | 23.5 | 20.25 |
| Max Vertical Height (H) (mm) | 9.0 | 7.9 | 6.8 |
| Max. Thickness (T) (mm) | 2.6 | 1.7 | 0.8 |

From the thickest sagittal plane at its horizontal midpoint, the anatomically-shaped lenticular aspect 401 to the right has a shape of equal, but opposite, conformation to that existing on the left. This is so that the anatomically-shaped lenticular aspect 401 will be wearable in the cul-de-sac of either eye, the left/right shape difference between conjunctival sacs of the two eyes having been shown to be minimal. The vertical height of the lenticular aspect (or thickness, T) (see FIG. 4A), another dimension noted in Table I, is maximum at the center of the lenticular aspect 401 and decreases left and right to the blunt lateral extremities. This is because the anatomically-shaped lenticular aspect 401 is somewhat meniscus-shaped in the facial plane, being more convex at its inferior edge and relatively flat horizontally at the superior edge. FIG. 4C is a front view of a contact lens 100 having an anatomically-shaped lenticular aspect 401 in a superior portion of the contact lens.

Additional non-limiting examples of anatomically-shaped lenticular aspects includes lenticular aspects having shapes that include round/oval, ellipse, triangular, heart shaped, square, pentagonal, diamond, pear shaped, rectangular, combinations thereof, and the like such that the lenticular aspect is shaped to fit into a conjunctival sac and attach to the upper eyelid of the wearer or to attach to the lower eyelid of the wearer using a fit between the lenticular aspect and an anatomical feature of the wearer.

Figure 5C:
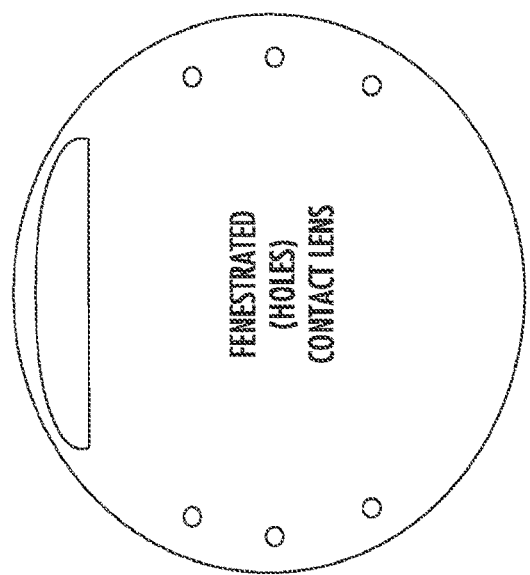
FIG. 5C is an illustration of a contact lens having a lenticular aspect that is fenestrated.
Figure 5B:
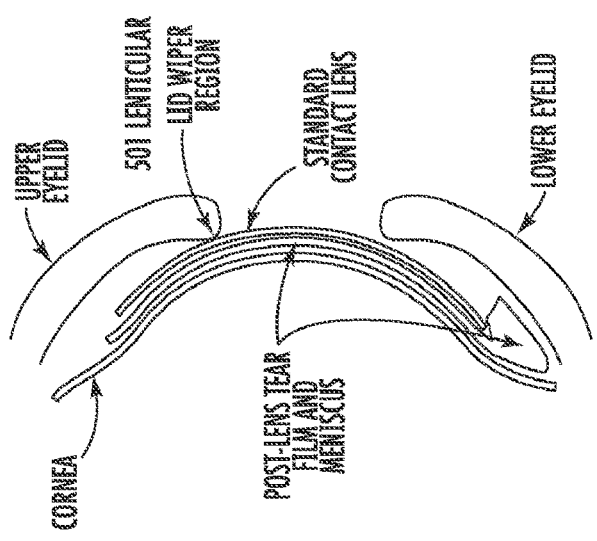
FIGS. 5A and 5B are profile images of eyes that illustrate the lid attachment fit of contact lens having a lenticular aspect in the superior portion of the lens as compared with a contact lens that does not have a lenticular aspect. In addition.
Figure 5A:
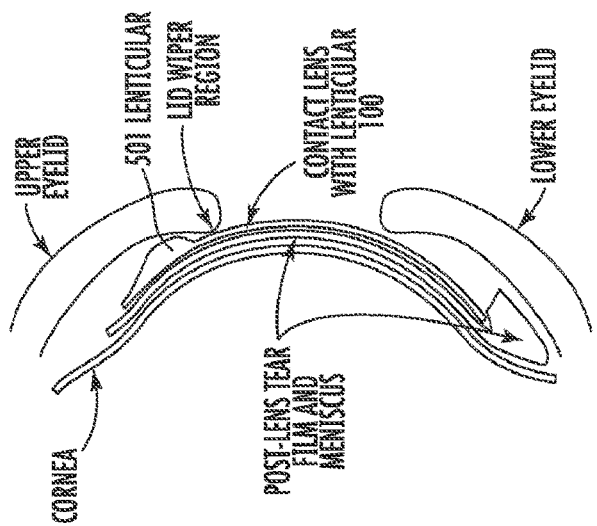

FIGS. 5A and 5B are exemplary profile images of eyes that illustrate the lid attachment fit of contact lens 100 having a lenticular aspect 501 in the superior portion of the lens as compared with a contact lens that does not have a lenticular aspect (FIG. 5B). In various embodiments, the lenticular aspect 501 shown in FIGS. 5A and 5B may be anatomically-shaped to attach to the upper eyelid by fitting within a conjunctival sac.

The contact lens embodiment shown in FIG. 5A is further configured to provide one or more of enhanced tear exchange, a greater tear layer thickness, or increased oxygen uptake of a cornea of a wearer. For example the lens may be a soft contact lens configured to provide the one or more of the enhanced tear exchange, the greater tear layer thickness, or the increased oxygen uptake of a cornea of the wearer by the contact lens having a shallow sagittal depth. Generally, the shallow sagittal depth comprises a sagittal depth that is less than a sagittal depth of a conventional soft contact lens. See, for example, Young, Graeme; "Mathematical Model for Evaluating Soft Contact Lens Fit;" Optometry and Vision Science, Vol. 81, No. 77 pp. e167-e176; 2014, which is fully incorporated by reference, for a discussion of sagittal ("sag") depths of contact lenses. In addition to the lenticular aspects described herein, other embodiments of the contact lenses described herein may have one or more grooves or channels in a surface of the contact lens that is in contact with the wearer's eye. Though the contact lens disclosed in these patents do not comprise a lenticular aspect, grooves or channels in the surface of the lens that is in contact with the eye are contemplated in U.S. Pat. Nos. 5,166,710 and 7,695,435 ("scalloped channels or circumferential fenestrated channels"), both of which are incorporated by reference. Holes and/or slits in the contact lens that allow for better oxygen exchange and perforated contact lens (though also without lenticular aspects as described herein) are contemplated in U.S. Pat. Nos. 5,104,213 and 4,666,267, both of which are incorporated by reference. Flexible contact lens for enhanced movement on the eye and therefore more tear exchange (though also without lenticular aspects) are contemplated in U.S. Pat. No. 4,896,958, which is incorporated by reference. However, each of the contact lens mentioned in these patents may have excessive movement within the eye of a wearer, which can affect the vision of the wearer and/or result in discomfort. For example, such contact lens (without a lenticular aspect as disclosed herein) may have movement in any direction of 1.5 mm, or more when in place on the wearer's eye. By the addition of a lenticular aspect as described herein to the contact lens, movement can be reduced to less than 1.5 mm and/or provide better centration of the contact lens thereby increasing comfort to the wearer and having less deleterious effects on vision while providing enhanced tear exchange, a greater tear layer thickness, and/or increased oxygen uptake of the cornea of the wearer. FIG. 5C is an illustration of a contact lens having a lenticular aspect that is fenestrated.

The use of a lenticular aspect on a soft contact lens in order to improve tear exchange also allows the contact lens to be fitted "flatter" (i.e., having lesser sagittal depth) in the central and/or peripheral aspect of the back surface of the contact lens than a conventional soft contact lens while still maintaining a comfortable fit. Such a soft contact lens includes a front-surface lenticular aspect or other symmetric or asymmetric area at a location on the front surface of the lens (a thicker region of any shape so long as it attaches to an anatomical feature (e.g., upper lid, lower lid, etc.) of a wearer). The purpose of the lenticular aspect is generally to attach the contact lens to the anatomical feature. Once the anatomical-feature attachment is achieved, that allows any region of the back surface of the soft contact lens to be fitted much flatter, or having less sagittal depth, than conventional soft contact lens. When lenses are fitted as such, more tears can exchange behind the contact lens, allowing debris and potential infection-causing and/or inflammatory agents to be washed away with each blink. The central back-surface radius of the contact lens may be 1.50 D to 3.00 D flatter than the central corneal curvature of the wearer, paired with additional flattening of peripheral back surface of the lens. The flatter lens design may include regions that are specifically designed to conform to the anatomy of the cornea and sclera, including a peripheral flattening of the back surface of the lens in the areas that cover the peripheral cornea and sclera. Traditional soft contact lenses, however, cannot be fitted especially flat because they are uncomfortable due to the excessive, uncontrolled movement and poor centration of the contact lens over the cornea. Because the embodiments of soft lens disclosed herein attach to an anatomical feature of the wearer, the lens movement is controlled by the attachment, rather than the movement of both lids and the movement of the eye, while the flatter, lower sagittal depth fitting back surface allows more tear exchange than the traditional, steeper-fitting back surface of conventional soft contact lens.

There are numerous benefits associated with soft contact lens with a lenticular aspect that have enhanced tear exchange, a greater tear layer thickness, and/or increased oxygen uptake of a cornea of a wearer. Such benefits may include, but are not limited to, allowing for improved: tear film; tear film thickness and quantity; tear film turnover behind the lens; tear film composition; corneal health and oxygen; conjunctiva health; goblet cell prevalence and density; dry eye signs and symptoms including conjunctival staining, tear osmolarity, impression cytology, tear protein analysis, Mucin assay test (tear ferning), ELISA tear protein profile; Lactoferrin Microepithelial defects/aqueous adequacy 40 sec.; Fluorescein Microepithelial defects/mucus deficiency; no staining visible Rose bengal/lissamine green; Impression cytology; Epithelial cell appearance/goblet cell density; uniform biomicroscopic appearance; total lysozyme reactivity (TLR); and the like.

Figure 6A:
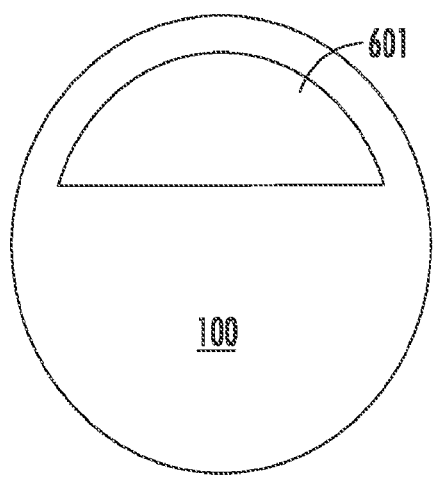
FIGS. 6A-6J illustrate front views of a contact lens having non-limiting examples of lenticular aspects as disclosed and described herein.
Figure 6B:
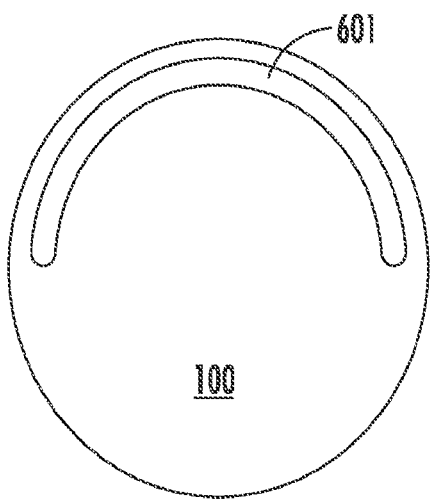
Figure 6C:
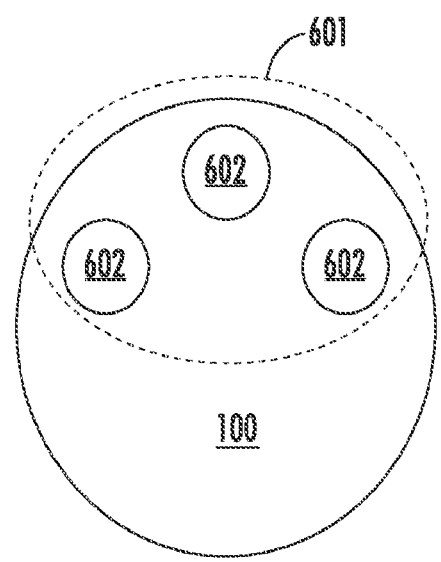
Figure 6D:
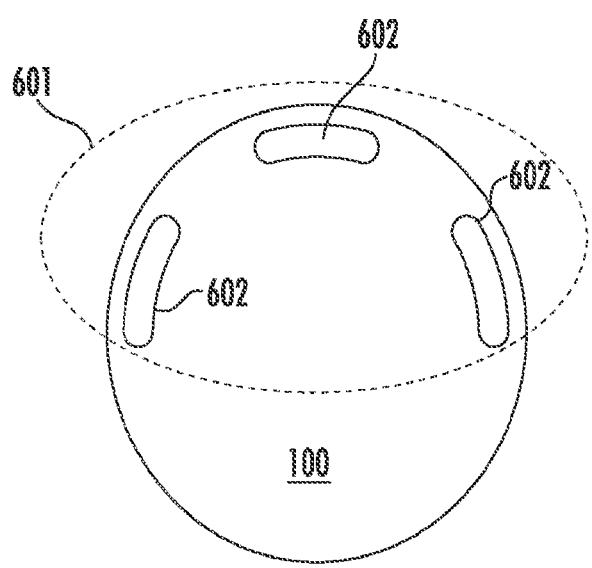
Figure 6E:
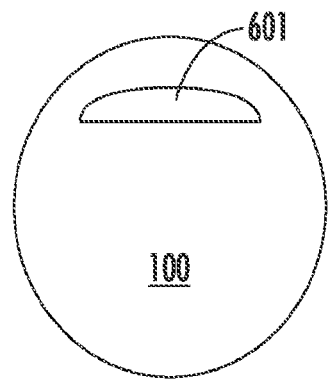
Figure 6F:
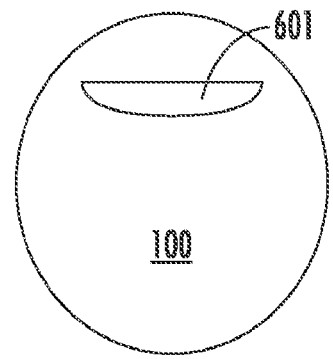
Figure 6G:
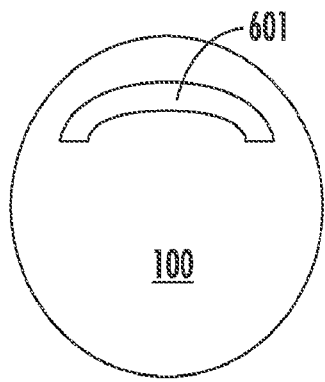
Figure 6H:
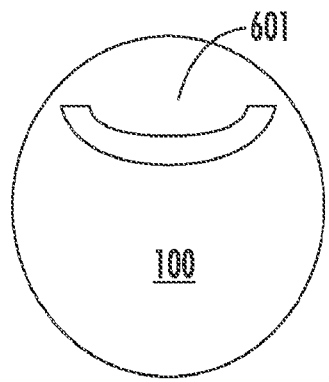
Figure 6I:
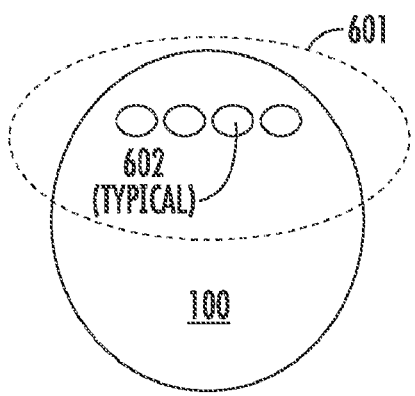
Figure 6J:
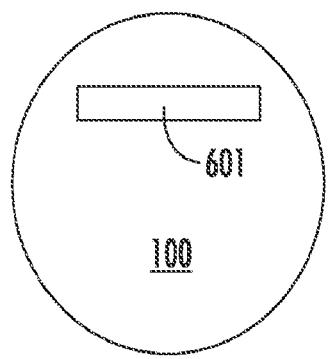

FIGS. 6A-6J illustrate front views of contact lens, including soft contact lens, having non-limiting examples of lenticular aspects in the superior portion of the contact lens as disclosed and described herein. It is to be appreciated that the lenticular regions of the embodiments shown in FIGS. 6A-6J have at least a portion of the lenticular aspect where the thickness of the lenticular aspect is greater than the thickness of the contact lens at its center portion. In FIG. 6A, the lenticular aspect 601 has a semicircular shape. In FIG. 6B, the lenticular aspect 601 has an arc shape. It is to be appreciated that the arc length can be shorter or longer that the length shown in FIG. 6B. In FIGS. 6C and 6D, the lenticular aspect 601 is comprised of a plurality of lenticular sections 602. For example, the lenticular aspect 601 of FIG. 6C is comprised of a plurality of semispherical sections on the superior portion of the contact lens and the lenticular aspect 601 of FIG. 6D is comprised of a plurality of arc sections. It is to be appreciated that the multi-section lenticular aspects of FIGS. 6C and 6D are exemplary and that other numbers of sections, shapes and sizes of lenticular aspects are contemplated within the scope of embodiments of the invention. FIGS. 6E-6J illustrate non-limiting examples of other shapes, sizes, positions and locations of lenticular aspects 601 that are contemplated within the scope of embodiments of the invention. Each of the embodiments shown herein may have, or may not have, prisms and/or ballasts in the inferior portion or other portions of the contact lens 100.

In some instances, the lenticular aspect 601 provides a fitting/alignment aid. When a contact lens 100 having a lenticular aspect 601 is held on the finger of a wearer in the process of placing the contact lens 100 in the eye, the lenticular aspect 100 can be seen through the contact lens 100, which allows for orientation of the contact lens 100. For example, with the portion of the contact lens 100 having the lenticular aspect 601 pointing away from the wearer when on the wearer's finger. The contact lens 100 is then inserted into the wearer's eye with the lenticular aspect 601 facing up.

Figure 7B:
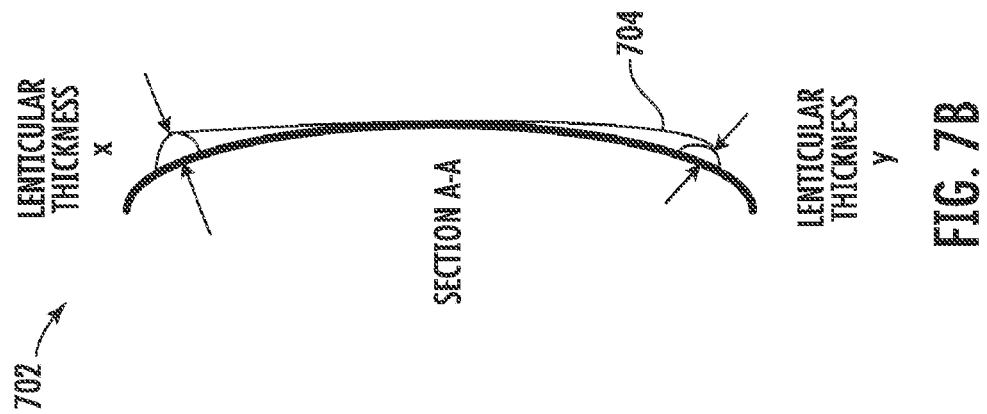
FIG. 7B illustrates Section A-A of FIG. 7A.
Figure 7A:
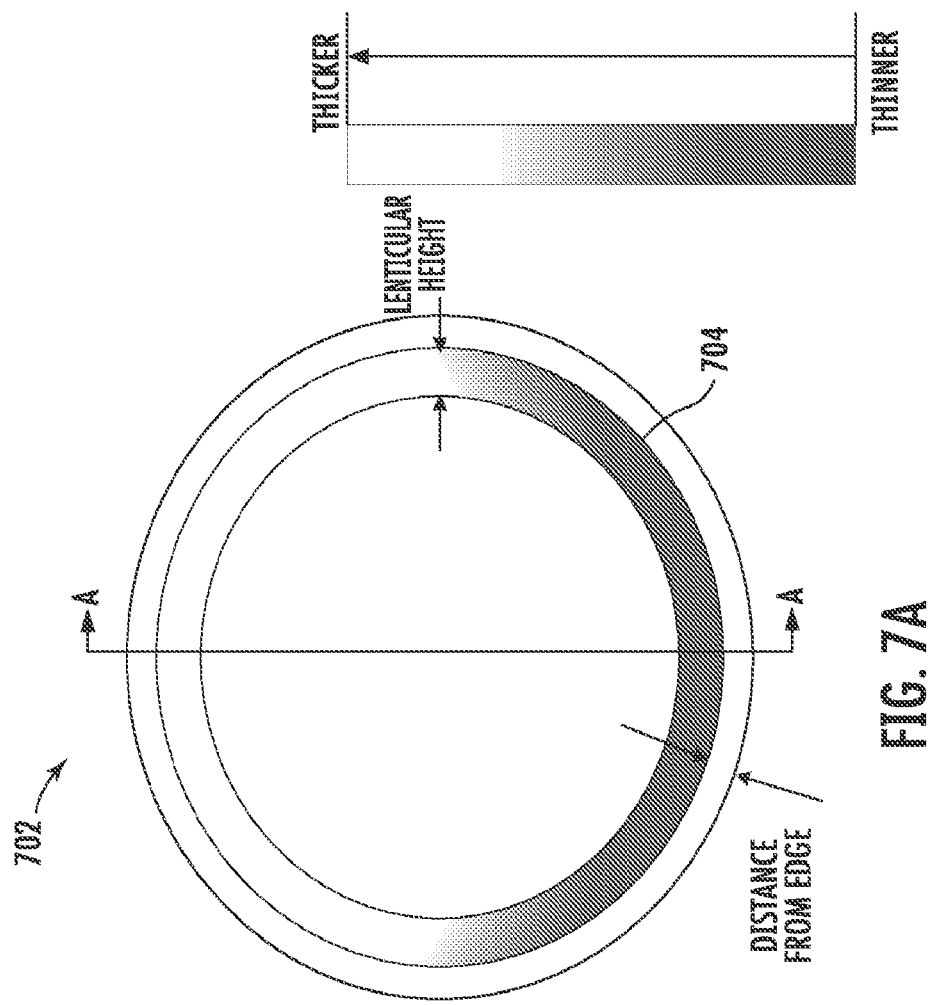
FIG. 7A is an illustration of a contact lens having a lenticular aspect of varying thickness that extends the full circumference of a contact lens.

FIG. 7A is an illustration of a contact lens 702 having a lenticular aspect 704 of varying thickness that extends the full circumference of the contact lens 702. The contact lens 702 may be any type of lens including soft, rigid gas permeable or hard lens including monovision, bifocal/multifocal, spherical, toric, disposable, daily-wear, extended wear, and the like. Though the contact lens 702 and the lenticular aspect 704 is shown in FIG. 7A as both being circular, it is to be appreciated that the contact lens 702 and/or the lenticular aspect 704 may have different shapes other than circular including oval, elliptical, rounded, and the like and it is to be appreciated the contact lens 702 may have one shape (e.g., elliptical) while the lenticular aspect 704 has a different shape (e.g., circular). In some instances, the lenticular aspect 704 has a thickness (T) that is consistent throughout the full radius of the lenticular aspect 704. In other instances, the thickness varies at different locations along the radius of the lenticular aspect 704. For example, as shown by the darkened portion of the lenticular aspect 704 in the upper portion of the contact lens 702 of FIG. 7A, the lenticular aspect 704 is thicker in the darker regions than it is in the lighter regions. This is further illustrated in FIG. 7B, which shows section A-A of FIG. 7A. As can be seen in FIG. 7B, the lenticular aspect 704 is thicker in the upper portion of the contact lens 702 than it is in the lower portion (lenticular thickness x is thicker than lenticular thickness y). While FIGS. 7A and 7B show two different thicknesses of the lenticular aspect 704 in different areas of its radius (upper portion and lower portion of the contact lens 702), it is to be appreciated that the lenticular aspect 704 can have multiple and varying thicknesses in various sections of its radius (it is not limited to only two thicknesses). In some instances, the lenticular aspect 704 that is the same or only slightly thicker than the portion of the contact lens 702 where it is attached, while in other instances the lenticular aspect 704 may have a thickness that is relatively thick compared to any other portion of the contact lens 702. For example, portions of the lenticular aspect 704 can be 0, 0.1, 0.2, 0.3, 0.4, 0.5, 0.6, 0.7, 0.8, 0.9, or 1.0 mm thicker than the remaining "non-thick" portion of the contact lens 702 or the thinner sections of the lenticular aspect 704. For example, the relatively thick area of the lenticular aspect 704 can comprise a thickest portion, which is 1.5 to 10 times thicker than another portion of the contact lens 702 or the thinner portions of the lenticular aspect 704. In other instances the lenticular aspect 704 may be thicker towards the edge of the contact lens 702 and taper in thickness towards the center of the contact lens 702, but still be displaced from the edge of the contact lens 702, or be thicker towards the center of the contact lens 702 and only taper towards the edge of the contact lens 702.

Also, while FIGS. 7A and 7B show that the distance that the lenticular aspect 704 is located a constant and consistent distance from the edge of the contact lens 702, it is to be appreciated that this is not a requirement and the distance from the edge may vary around the circumference of the contact lens 702. Generally, the location of the lenticular on the lens is designed to place it in a location that allows for lid attachment (i.e., far enough from the center of the contact lens such that the lenticular can be placed under the upper lid). This is illustrated in FIG. 7C. For example, at various locations along the radius of the lenticular aspect 704 an edge of the lenticular aspect closest to an outer edge of the contact lens ("distance from edge") may vary along the length of the lenticular aspect 704 from 0, 0.1, 0.2, 0.3, 0.4, 0.5, 0.6, 0.7, 0.8, 0.9, 1.0, 1.5, 2.0, 2.5, 3.0, 3.5, 4.0, 4.5, or 5.0 millimeters away from the outer edge of the superior portion of the contact lens. Distance from edge may also depend on diameter of the contact lens. For example, a lens with a diameter of 14.0 mm may have a lenticular that needs to be placed 5.0 mm from the center of the contact lens in order to be under the upper lid, and that lenticular will therefore be 2.0 mm from the edge of the contact lens. If the same lens is manufactured at an overall diameter of 17.0 mm, the lenticular will be placed 3.5 mm from the edge of the contact lens. Furthermore, FIGS. 7A and 7B show that the lenticular aspect 704 has a consistent lenticular height across the full radius of the lenticular aspect 704. It is to be appreciated that the lenticular height may vary along the radius of the lenticular aspect 704, as shown in FIG. 7C. As can be seen in FIG. 7C, lenticular height a is greater than lenticular height b. In FIG. 7C, the lenticular aspect 704 varies in thickness (shown by the darker sections of the lenticular aspect 704), distance from the edge of the contact lens 702, and lenticular height along the radius of the lenticular aspect 704; however, it is to be appreciated that all three dimensions are not required to vary along the radius of the lenticular aspect, only one of the dimensions (thickness, distance from edge, and lenticular height) may vary along the radius while the other two remain constant, or in some instances two of the dimensions may vary along the radius of the lenticular aspect 704 while the third remains constant.

In some instances, the lenticular aspect having varying dimensions does not extend the full circumference of the contact lens, as shown in FIG. 7D. In such instances, the lenticular aspect 706 extends only a portion of the circumference of the contact lens 708, but varies in one or more of thickness, distance from edge and lenticular height along the distance it does extend along the portion of the circumference of the contact lens 708 that it does extend.

FIGS. 8A and 8B are grey-scale illustrations of a contact lens 800 having a superior lenticular aspect 802, and further comprising one or more ballast regions 804. Though shown in FIGS. 8A and 8B in the lower portion and/or the middle of the contact lens, it is to be appreciated that this disclosure contemplates any number of ballast zones at any location on the contact lens. For example, this includes one or more ballast zones that extend from the periphery towards the center of the lens a specific amount but do not interfere with the optical zone/ballast zones that extend superiorly and inferiorly from that center point to accomplish the desired effect of centration and rotational stability. In FIG. 8A, the ballast regions 804 are located at the 3:00 and 9:00 o'clock positions on the contact lens 800. In FIG. 8B, the ballast regions 804 are shown located at the 4:00 and 8:00 o'clock positions. These locations are exemplary, and it is to be appreciated that the ballast regions 804 can be located at different locations than are shown in FIGS. 8A and 8B, and there may be more or fewer ballast regions 804 than the embodiments shown in FIGS. 8A and 8B. It is also to be appreciated that the location and dimensions of the lenticular aspect 802 shown in FIGS. 8A and 8B are exemplary too, and it is contemplated that within the scope of this invention the lenticular aspect 802 may have different locations and/or designs, as described herein. As shown in FIGS. 8A and 8B, the contact lens 800 comprises a superior lenticular aspect 802 located in a central, upper portion of the lens 800 and shaped to interact with an upper tarsal plate of an upper eyelid of a wearer such that the contact lens 800 translates upward in a downgaze of the wearer to place a viewing zone of the contact lens 800 over a pupil or cornea of the wearer. In the examples shown in FIGS. 8A and 8B, the one or more ballast regions 804 change one or both of the center of gravity (COG) and/or the center of mass (COM) of the contact lens 800 from what it would be without the one or more ballast regions 804. Generally, the one or more ballast zones 804 comprise a mass located in the lower half (inferior) portion of the contact lens 800. The number, size, location, dimensions, and mass (weight) of the ballast regions can be changed based on the desire for positioning the contact lens 800 on the wearer's eye. The mass of each of the one or more ballast zones can be selected to locate a center of mass or a center of gravity of the contact lens to either raise, i.e., higher center of gravity, or lower, i.e., lower center of gravity, the position of the contact lens on the eye. The ballast zones 804 can provide a counter-balance to a superior lenticular aspect, thus providing a more comfortable and better fit to the contact lens 800. Furthermore, the lenticular aspect 802 and/or the ballast zones 804 provide rotational stabilization to the contact lens 800. The rotational stability is provided by the positioning the margin of the upper eyelid between the superior lenticular aspect 802 and the ballast zones 804. This helps to prevent the dislocation of the lenticular aspect 802 from underneath the upper eye lid, i,e, keep the lenticular lid-attached, and also helps prevent clockwise or counter-clockwise rotation of the contact lens during a blink. Clinically, this allows a fit of a toric and/or bifocal/progressive addition multifocal lenses that requires less adjustments for a lens that is rotated clockwise or counter-clockwise.

Though not shown in FIGS. 8A and 8B, it is to be appreciated that the scope of embodiments of this invention are also directed to contact lens having ballast zones that are used to establish a desired COG/COB, and the contact lens does not have a lenticular aspect.

While the ballast zones 804 are generally comprised of the same material that the contact lens 800 is comprised of, it is to be appreciated that in some instances the one or more ballast zones 804 may be comprised of materials different than the contact lens. For example, the contact lens 800 may be comprised of hard or rigid material, while the one or more ballast zones 804 may be comprised of soft polymeric material.

In any one of the contact lens shown in FIGS. 7A-8B, it is to be appreciated that the lenticular aspect, or at least a portion of it can be configured to anatomically fit with an anatomical feature of a wearer. For example, the lenticular aspect, or at least a portion of it can be configured to attach to the upper tarsal plate of a wearer by the lenticular aspect (or portion of it) fitting with in the Kessing's Space of the wearer.

Figure 9:
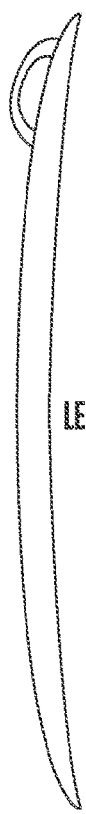
FIG. 9 is a side-view illustration of a contact lens having a lenticular compartment.

In some instances, one or more of the lenticular aspects, prisms, and/or ballast zones can serve as compartments for the contact lens wherein at least a portion of the lenticular aspect, prism, and/or ballast zone creates a hollow "pocket" in which various materials, substances, devices can be carried "onboard" the contact lens. FIG. 9 is a side-view illustration of a contact lens having a lenticular compartment. In some instances, materials, substances, devices, and the like placed in the compartment are sealed in the compartment with no opening for entering or leaving the compartment. In other instances, one or more openings may exist in the compartments so that materials, substances, devices, and the like places in the compartment may have access to either the front (outer) side of the contact lens or the inner (eye) side of the contact lens. For example, compartments in one or more of the lenticular aspect, prism, or ballast zones can be used to house the electronics, antenna, cooling mechanisms, etc. for using the contact lens for displaying electronically-generated and/or virtual optically displayed images. In other instances the compartments in one or more of the lenticular aspect, prism, or ballast zones can be used to house sensors, including for example sensors that sense biological information about the eye. In yet other instances, the compartment in one or more of the lenticular aspects, prisms, and/or ballast zones is used to hold a liquid and/or viscous substance such as a medicine or wetting-agent for the eye. For example, the compartment in one or more of the lenticular aspects, prisms, and/or ballast zones may be used in some instances to hold and gradually release into the eye, Cyclosporin A, which is used to treat chronic dry eye. In some instances, the opening from the compartment is dimensioned such that the medicine or wetting-agent is gradually dispersed into the eye over time. In other instances, the opening may include a membrane that controls the flow of the liquid or viscous substance into the eye. In other instances, the compartment in one or more of the lenticular aspects, prisms, and/or ballast zones may hold a solid and/or powdery substance that may also be a medicine or some form of treatment of the eye where the solid or powdery substance is exposed to the natural moisture of the eye through one or more opening or membranes such that the solid or powdery material is dissolved by the moisture of the eye and dispersed into the eye.

Figure 10A:
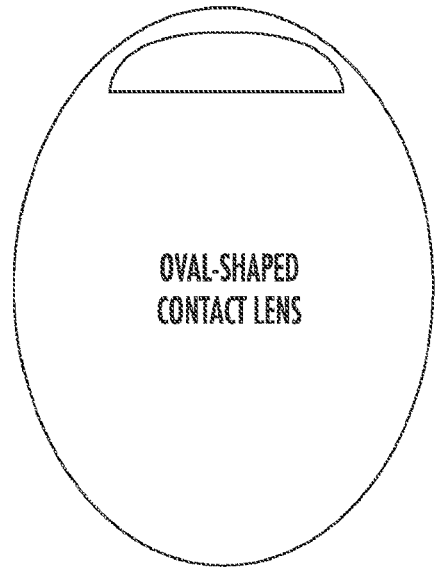
FIG. 10A is an illustration of an exemplary oval contact lens having a lenticular aspect.
Figure 10B:
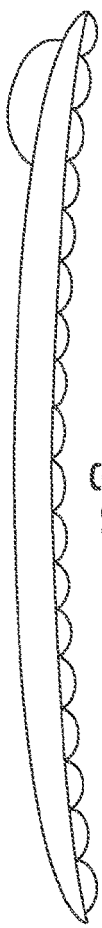
FIG. 10B is an illustration of a side view of an exemplary contact lens having scalloped edges.

The above-described contact lenses have generally been described as having a round outer edge/overall shape. Nonetheless, it is to be appreciated that the outer-edge/overall shape of the contact lens can be configured in shapes other than round. For example, the outer edge of the lens may form a contact lens having an oval, elliptical, or other shape. FIG. 10A is an illustration of an exemplary oval contact lens having a lenticular aspect. Furthermore, the outer edges of the contact lens may not be smooth but may have shaped edges including for example scalloped edges, jagged edges, zig-zag edges, and the like. FIG. 10B is an illustration of a side view of an exemplary contact lens having scalloped edges. Such configurations may have an aesthetic effect, as well as providing one or more of an enhanced tear exchange, a greater tear layer thickness, or increased oxygen uptake of a cornea of a wearer.

In yet other embodiments, a contact lens that comprises a lenticular aspect is provided, that further includes holographic, painted, printed, and/or etched portions. For example, the embodiments of a contact lens as shown in FIGS. 1A-8B, and as described herein, having a lenticular aspect having a length and extending along at least a portion of the circumference of the contact lens that varies in at least one of thickness, distance from the edge, or lenticular height along its length provides centration and rotational stability so that marking/impressions made on the contact lens surface would center over the pupil and maintain the intended image or marking in ways not possible on conventional rigid gas permeable and soft contact lenses. These contact lenses having the lenticular aspect may, in some instances, further comprise ballast zones 804 as described with reference to FIGS. 8A and 8B.

The contact lens may include a holographic design, either through laser ablation or nickel embossing, to simulate an iris and or pupil on the surface of the contact lens for cosmetic or therapeutic uses. Such uses may include, but are not limited to: (1) Using a holographic design to match or otherwise enhance the iris color and pupil of one or more eyes on an individual for cosmetic or therapeutic effect. For example, the movie and theater industry utilize these lenses for special effects. (2) For use to mask or camouflage conditions like aniridia, pupil irregularities, and permanent eye damage, to improve the appearance and improve the quality of life for the patient. (3) Eliminating Double Vision/Occluder Lenses: Occluder lenses are often preferable to an eye patch for eliminating double vision or diplopia. It is important to design the lens so that the black pupil is large enough to totally block out light (typically 2-3 mm larger than the maximum pupil size). Provide solid black pupil lenses (clear outer edge) with various pupil sizes. (4) Eliminating Photophobia: Prosthetic iris lens designs with a clear pupil opening to recreate a normal pupil size, thereby eliminating uncomfortable light sensitivity from conditions resulting in large or oblong pupil. Trauma commonly causes complications to the iris and an irregular pupil opening. (5) Enhancing Contrast/Vision: Colored contact lenses can be used as an effect to reduce light sensitivity; some can enhance contrast through various color tints (often for sports using gray, green, or amber). In addition, professional athletes may wear sport tint lenses to enhance their visual performance. (6) Color Vision Benefits: Red other color lenses (for certain color deficiencies).

Cosmetic application of colored holographic contact lens includes, but is not limited to: (1) Changing the color or size of the iris and/or pupil. (2) Add a design/logo or shape to the iris or ocular surface. (3) Allowing the wearer to select from any pantone color or mix of pantone colors. (4) Matching the iris and pupil pattern via digital photography and scanning of the pixel level RGB data to simulate the Iris and pupil of the patient's healthy eye. Natural lighting conditions are used when photographing the iris color for best matching.

The holographic design may also be used for lens marking. For example, marking the lens with holographic for orientation marks at locations on the face of the lens. Also, a holographic design can be used for marking a specific feature on the contact lens, i.e. a bump or lenticular.

In some instances, using a larger lens diameter provides better centration and maximize cosmetic and therapeutic effects. Typical contact lens have a diameter that ranges from 5 mm to 15 mm, but can be smaller or larger. For example, the contact lens may have a diameter of 17 mm or larger.

Contact lens, such as those described herein, can also be marked with a laser or etching tool to identify specific aspects of the lens, i.e. bump or the lenticular aspect, and/or to identify the design specifications of the lens on the lens itself.

In another aspect, a contact lens that comprises a lenticular aspect is provided, that further includes tinting all or a portion of the contact lens. Such a tinted contact lens with lenticular aspect provides enhancement of vision for athletics and recreation. In various embodiments, all or a portion of the lens is tinted with specific colors to block specific wavelengths of light. The tint may be applied to the surface of the contact lens (front and/or back surface), or it can be mixed into the substance used to form the contact lens. Tinting can also enhance contrast/vision. A tinted contact lens can be used as an effect to reduce light sensitivity; some can enhance contrast through various color tints (often for sports using gray, green, or amber). In addition, professional athletes may wear sport tint lenses to enhance their visual performance. Use of the lenticular aspect, which provides centration and rotational stability of the contact lens, allows portions of the lens to be tinted darker while other portions are less tinted or not tinted at all. For example, a contact lens having a lenticular may be shaded darker at the top, superior portion of the lens with the shading gradually lessened moving toward the bottom, inferior portion of the contact lens; or vice-versa. Similarly, the shading can increase/decrease from an inside (anterior) portion of the lens to an outside (posterior) portion, and vice-versa.

In yet another aspect, a contact lens that comprises a lenticular aspect is provided, that further includes polarization of all or a portion of the contact lens. Polarization of a contact lens has not been possible until now as there has been a lack of ability to lock the rotation of the lens. Here, the centration and rotational stability provided by a contact lens having a lenticular aspect allows the axis of polarization to remain constant allowing consistent polarization of light. The addition of ballast zones (described herein) to the contact lens further enhances centration and rotational stability for polarization.

Also disclosed herein are methods of making contact lenses. For example, disclosed is a method of making a contact lens, the method comprising manufacturing a contact lens comprising forming a lenticular in a portion of the lens. The contact lens can further comprise a base down prism or a ballast zones in the inferior portion of the lens. In one example, the base down prism and/or ballast zones are added to the lens in a second step of a manufacturing process. In some instances, the lenticular aspect is added in a second or third step of a manufacturing process. The lenticular aspect may be located in a superior portion of the contact lens and be shaped to interact with an upper tarsal plate of an upper eyelid of a wearer such that the contact lens translates upward in a downgaze of the wearer to place a viewing zone of the contact lens over a pupil or cornea of the wearer and the superior lenticular aspect provides rotational stabilization to the contact lens; and/or the lenticular aspect may have a length and extend along at least a portion of the circumference of the contact lens, and the lenticular aspect varies in at least one of thickness, distance from the edge, or lenticular height along its length. In some instances, the contact lens, either hard or soft, is fully molded except the optical zone. The optical zone is lathed at a later time to customize the optics for the individual.

Also disclosed is a method of treating an individual in need of vision correction, the method comprising dispensing the soft contact lens disclosed herein to the individual, thereby treating the individual in need of vision correction. In one example, the individual has been diagnosed with ametropia (e.g., astigmatism, myopia, hyperopia). In another example, the individual has been diagnosed with presbyopia, another accommodative disorder, and/or a binocular vision disorder. For example, one or more surfaces of embodiment of the contact lens described herein can be made toric (to treat astigmatism), and/or a flatter or a steeper front surface can be formed in the embodiments of contact lens described herein (to correct either myopia or hyperopia), and/or a bifocal/trifocal/multifocal/progressive addition bifocal change in power can be formed in the bottom (inferior portion) of the lens to treat presbyopia. Furthermore, the lens described herein having a lenticular aspect can be used to center and orient optics of a contact lens that is used for myopia control.

Further disclosed is a method of determining physical characteristics of a contact lens for a person at one point in that person's lifetime. Physical characteristics can include but are not limited to one or more of lens diameter, lens shape, sagittal depth of the lens, lenticular aspect thickness, lenticular aspect distance from edge, lenticular aspect height, lenticular aspect length, ballast zone size, weight and location, lens tinting, and the like. The physical characteristics are determined to provide comfort of the contact lens when in the wearer's eye and also fit of the lens in the wearer's eye to provide centration, rotational stability, and to translate the contact lens upwards in a downgaze of the wearer or holding the contact lens in an upwards position as a wearer's eye moves downwards behind the contact lens. Physical characteristics also determine whether the contact lens is a spherical, toric, presbyopic, or toric presbyopic contact lens. Because such a lens can be a spherical, toric, presbyopic, or toric presbyopic lens, it is a potential platform lens across a person's lifetime. These physical characteristics of the contact lens are recorded for that person. The person is also initially prescribed certain optical characteristics of the lens (i.e., the optical zone is designed and created with characteristics that improves and/or maintains the wearer's vision). Generally, optical characteristics change over time as a person ages, but many of the physical characteristics of the lens remains the same throughout a person's lifetime. Rather than having to redesign the entire lens each time a person's optical characteristics change, the method contemplates only changing the optical characteristics of the prescribed lens while the physical characteristics remains the same. For example, a contact lens can be designed that has the desired physical characteristics, and then the contact lens, either hard or soft, is fully molded except the optical zone. The optical zone is lathed at a later time to customize the optics for the individual.

As used in the specification, and in the appended claims, the singular forms "a," "an," "the," include plural referents unless the context clearly dictates otherwise.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A contact lens comprising:
a superior portion of the contact lens;
an inferior portion of the contact lens;
a lens portion;
an edge extending a circumference of the contact lens; and
a lenticular aspect having a length and extending the circumference of the contact lens, wherein the lenticular aspect has dimensions of a thickness, a distance from the edge, and a lenticular height, wherein each of the dimensions of the lenticular aspect vary along the length of the lenticular aspect; and
wherein at least a portion of the lenticular aspect is shaped to interact with an upper tarsal plate of an upper eyelid of a wearer, said interaction translating the contact lens upwards in a downgaze of the wearer or holding the contact lens in an upwards position as a wearer's eye moves downwards behind the contact lens.

2. The contact lens of claim 1, wherein the lens portion is an optical zone and wherein the portion of the lenticular aspect that is shaped to interact with the upper tarsal plate of the upper eyelid of the wearer translates the contact lens upwards in the downgaze of the wearer such that at least a portion of the optical zone is maintained over a pupil of the wearer's eye, said optical zone comprising one of single-vision, bifocal, trifocal, progressive addition bifocal, multifocal, and/or toric.

3. The contact lens of claim 1, wherein the contact lens is a soft contact lens.

4. The contact lens of claim 1, wherein the contact lens is a rigid gas permeable contact lens or a hybrid contact lens.

5. The contact lens of claim 1, wherein the contact lens further comprises one or more ballast zones.

6. The contact lens of claim 5, wherein each of the one or more ballast zones have a mass and the mass of each of the one or more ballast zones is selected to locate a center of mass or a center of gravity of the contact lens.

7. The contact lens of claim 5, wherein the contact lens further comprises a base down prism located at least partially in an inferior portion of the contact lens.

8. The contact lens of claim 7, wherein at least one of the lenticular aspect, the one or more ballast zones, or the base down prism includes one or more compartments.

9. The contact lens of claim 8, wherein the one or more compartments are comprised of at least a portion of the lenticular aspect, prism, and/or ballast zones having a hollow pocket in which various materials, substances, or devices can be carried onboard the contact lens.

10. The contact lens of claim 9, wherein the materials, substances, or devices placed in the one or more compartments are sealed in at least one of the one or more compartments with no opening for entering or leaving the sealed compartment.

11. The contact lens of claim 9, wherein one or more openings exist in at least one of the one or more compartments so that the materials, substances, or devices placed in the compartment having the one or more openings have access to either a front (outer) side of the contact lens or an inner (eye) side of the contact lens.

12. The contact lens of claim 11, wherein at least one of the one or more compartments is used to hold a liquid and/or viscous substance such as a medicine or wetting-agent for the eye.

13. The contact lens of claim 12, wherein the one or more openings from the at least one compartment is dimensioned such that the medicine or wetting-agent is gradually dispersed into an eye of the wearer over time.

14. The contact lens of claim 12, wherein the one or more openings from the at least one compartment include a membrane that controls a flow of the liquid or viscous substance into the eye.

15. The contact lens of claim 12, wherein the one or more compartments is used to hold Cyclosporin A, which is gradually released into the eye to treat chronic dry-eye.

16. The contact lens of claim 11, wherein at least one of the one or more compartments holds a solid and/or powdery substance.

17. The contact lens of claim 16, wherein the solid or powdery substance is exposed to natural moisture of a wearer's eye through the one or more opening or through a membrane that allows moisture entry into the at least one compartment such that the solid or powdery material is dissolved by the moisture of the eye and dispersed into the eye.

18. The contact lens of claim 8, wherein at least one of the one or more compartments is used to house electronics, antenna, or cooling mechanisms for using the contact lens for displaying electronically-generated and/or virtual optically displayed images or for sensing biological information about the eye.

19. The contact lens of claim 1, wherein the edge extending the circumference of the contact lens forms a contact lens having a shape, said shape forming a contact lens that is round or a contact lens that is not round, said shape selected to provide a cosmetic effect or to provide one or more of an enhanced tear exchange, a greater tear layer thickness, or increased oxygen uptake of a cornea of a wearer.

20. The contact lens of claim 19, wherein the shape of the contact lens is an oval or elliptical shape.

21. The contact lens of claim 1, wherein the edge extending the circumference of the contact lens is shaped comprising a scalloped, jagged, or a zig-zag shape, said shape selected to provide a cosmetic effect or to provide one or more of an enhanced tear exchange, a greater tear layer thickness, or increased oxygen uptake of a cornea of a wearer.

22. The contact lens of claim 1, wherein the lenticular aspect interacts with a palpebral conjunctiva and an upper tarsal plate that lies below the palpebral conjunctiva to provide centration of the contact lens on a wearer's eye and rotational stability of the contact lens on the wearer's eye.

23. A contact lens comprising:
an edge extending a circumference of the contact lens; and
a lenticular aspect having a length and extending the circumference of the contact lens, wherein the lenticular aspect has dimensions of a thickness, a distance from the edge, and a lenticular height,
wherein each of the dimensions of the lenticular aspect vary along the length of the lenticular aspect, and
wherein the lenticular aspect interacts with a palpebral conjunctiva and an upper tarsal plate that lies below the palpebral conjunctiva to provide centration of the contact lens on a wearer's eye and rotational stability of the contact lens on the wearer's eye.

24. A contact lens comprising:
- an edge extending a circumference of the contact lens;
- a lenticular aspect having a length and extending the circumference of the contact lens, wherein the lenticular aspect has dimensions of a thickness, a distance from the edge, and a lenticular height, wherein each of the dimensions of the lenticular aspect vary along the length of the lenticular aspect;
- one or more ballast zones; and
- a base down prism located at least partially in an inferior portion of the contact lens, wherein at least one of the lenticular aspect, the one or more ballast zones, or the base down prism includes one or more compartments.

\* \* \* \* \*